United States Patent
Sato

(10) Patent No.: US 9,404,866 B2
(45) Date of Patent: Aug. 2, 2016

(54) FLUORESCENT LIGHT OBSERVATION DEVICE AND FLUORESCENT LIGHT OBSERVATION METHOD

(75) Inventor: Takayuki Sato, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 147 days.

(21) Appl. No.: 14/348,064

(22) PCT Filed: Jul. 13, 2012

(86) PCT No.: PCT/JP2012/067978
§ 371 (c)(1),
(2), (4) Date: Mar. 28, 2014

(87) PCT Pub. No.: WO2013/051317
PCT Pub. Date: Apr. 11, 2013

(65) Prior Publication Data
US 2014/0254953 A1    Sep. 11, 2014

(30) Foreign Application Priority Data

Oct. 3, 2011   (JP) .................................. 2011-219168

(51) Int. Cl.
*G01N 21/64* (2006.01)
*G01N 21/91* (2006.01)
*G01N 21/17* (2006.01)

(52) U.S. Cl.
CPC ............ *G01N 21/6456* (2013.01); *G01N 21/91* (2013.01); *G01N 2021/1765* (2013.01); *G06T 2207/20024* (2013.01); *G06T 2207/20224* (2013.01)

(58) Field of Classification Search
None
See application file for complete search history.

(56) References Cited

U.S. PATENT DOCUMENTS

| 6,026,319 | A | 2/2000 | Hayashi | |
|---|---|---|---|---|
| 2005/0242296 | A1* | 11/2005 | Kleinerman | G01J 1/58 250/458.1 |
| 2006/0149133 | A1 | 7/2006 | Sugimoto et al. | |
| 2008/0198368 | A1* | 8/2008 | Matsumoto | G01N 21/6452 356/73 |
| 2008/0239070 | A1* | 10/2008 | Westwick | A61B 1/045 348/68 |
| 2010/0013953 | A1 | 1/2010 | Niikura | |
| 2011/0104071 | A1* | 5/2011 | Lee | A61B 5/0071 424/9.6 |
| 2012/0133904 | A1* | 5/2012 | Akiyama | G02B 27/102 353/38 |

FOREIGN PATENT DOCUMENTS

| CN | 101424569 | 5/2009 |
|---|---|---|
| CN | 101802675 | 8/2010 |
| DE | 10 2006 042 670 | 3/2007 |
| EP | 2 213 222 | 8/2010 |
| JP | H07-155292 A | 6/1995 |
| JP | H09-131306 A | 5/1997 |
| JP | H10-151104 A | 6/1998 |
| JP | H11-308533 A | 11/1999 |
| JP | 2001-083432 A | 3/2001 |
| JP | 2002-098900 A | 4/2002 |
| WO | WO 2010/032452 | 3/2010 |

* cited by examiner

*Primary Examiner* — Utpal Shah
*Assistant Examiner* — Kate R Duffy
(74) *Attorney, Agent, or Firm* — Drinker Biddle & Reath LLP

(57) ABSTRACT

A fluorescence observation device includes a light source supplying excitation light, an interlaced imaging device, a field memory storing an image output from the imaging device, and a difference computing unit generating a difference image. The light source supplies the excitation light such that one of the first and second field image acquiring periods in the imaging device is a fluorescence image acquiring period, and the other is a background image acquiring period. The difference computing unit switches between a first mode of subtracting a background image of the memory from a fluorescence image output from the imaging device, and a second mode of subtracting a background image output from the imaging device from a fluorescence image of the memory, to apply the mode. Accordingly, it is possible to generate images in which fluorescence is extracted in real time.

16 Claims, 13 Drawing Sheets

Fig.5
(a)
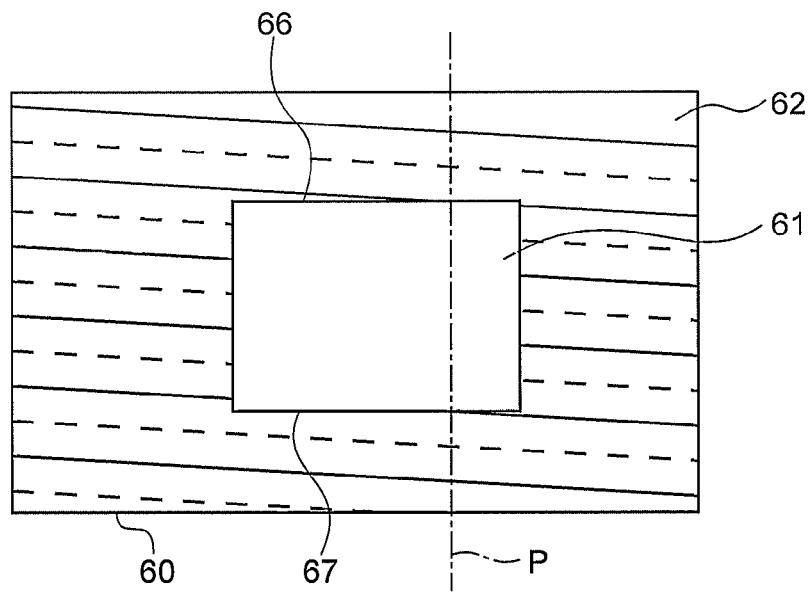
(b)
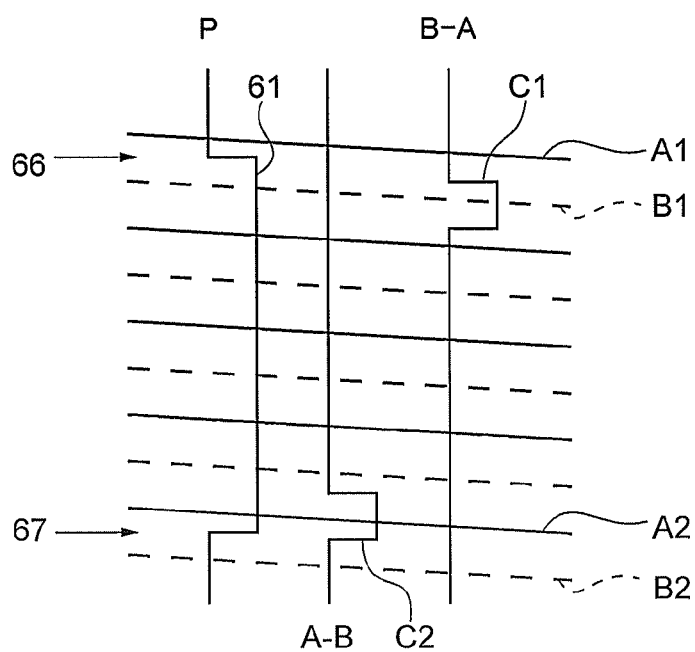

Fig.6
(a)
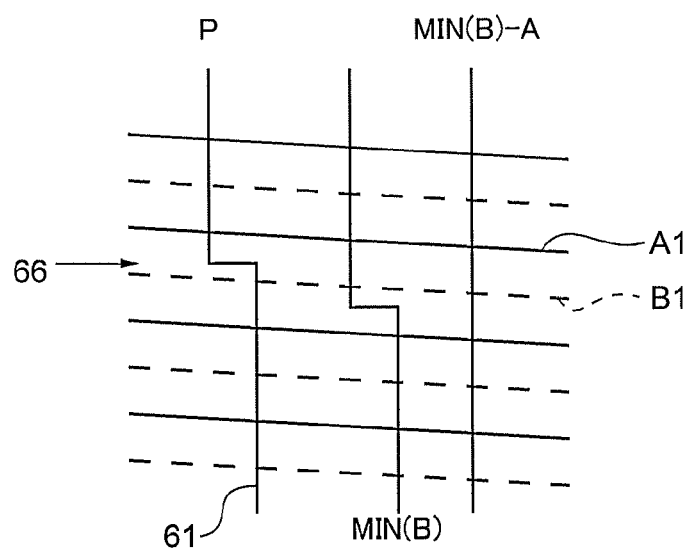
(b)
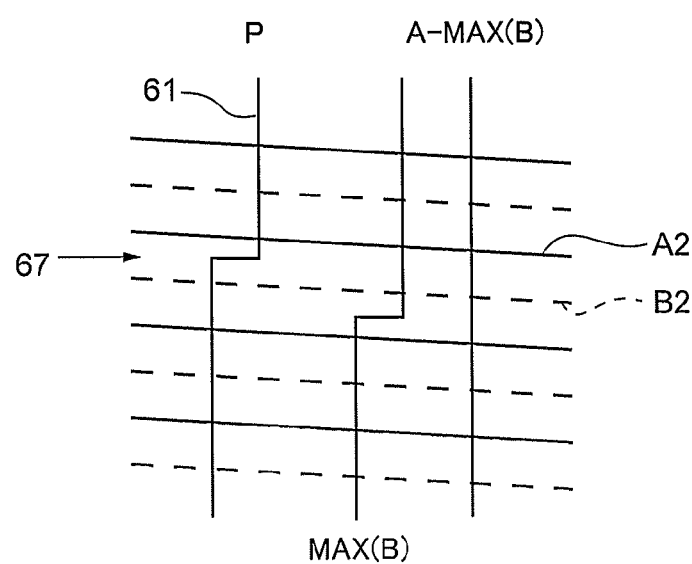

Fig.8
(a)
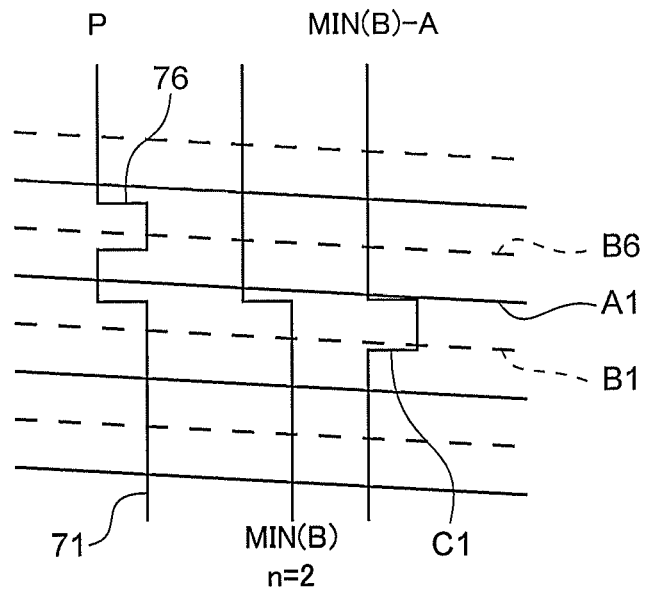
(b)
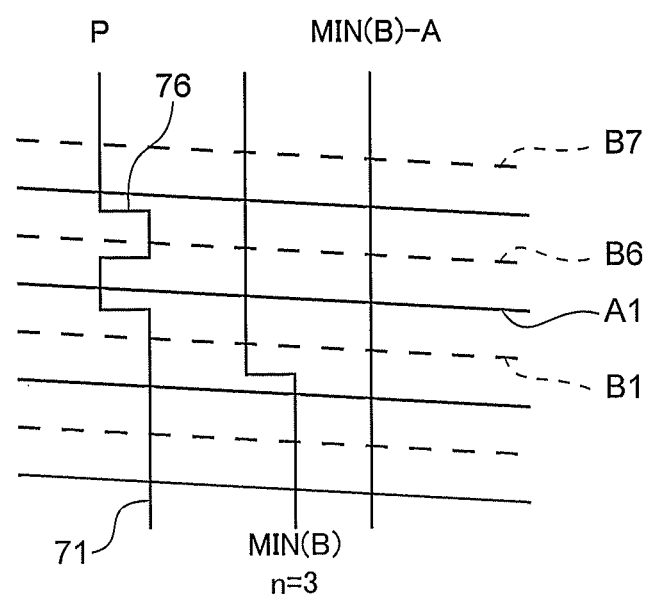

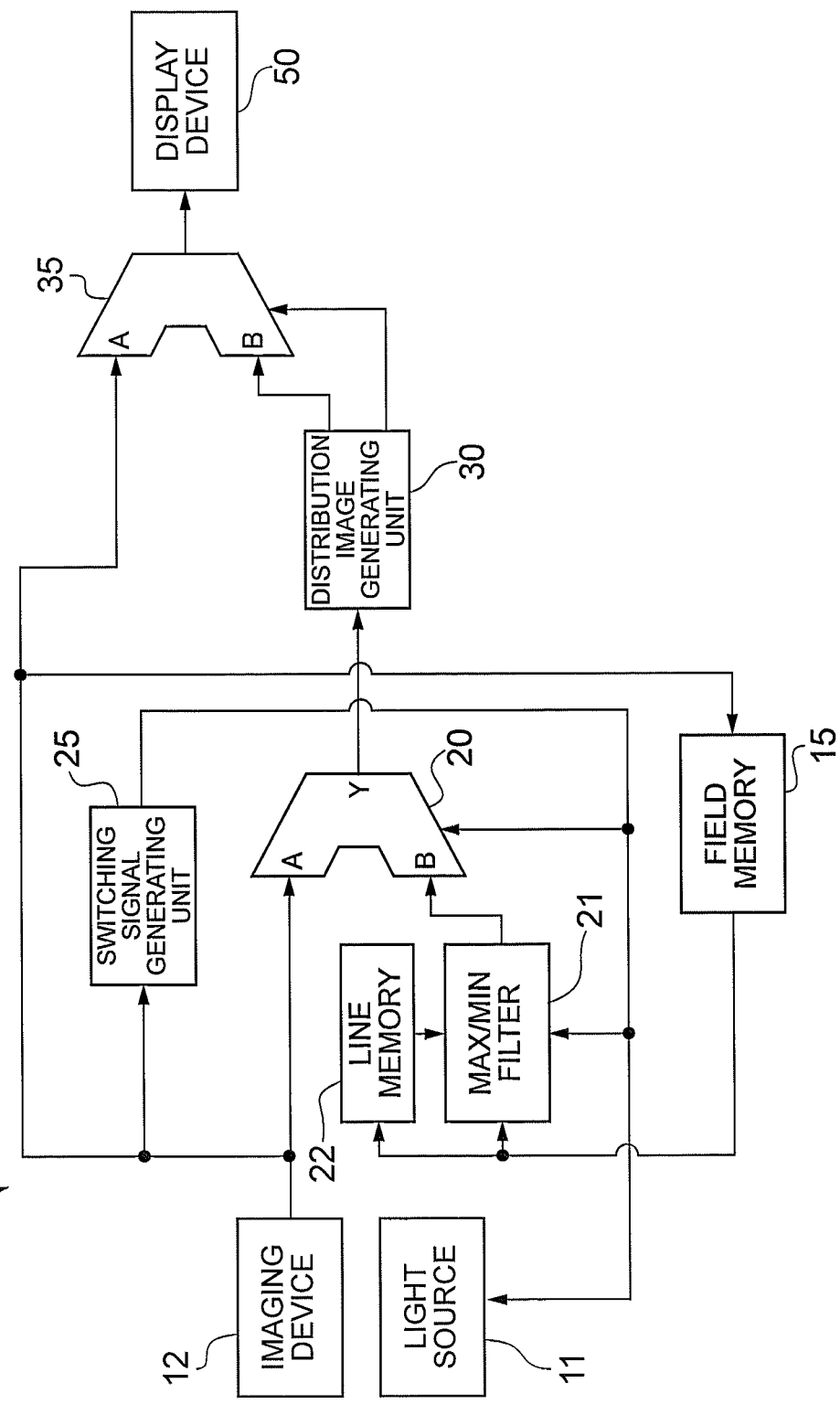

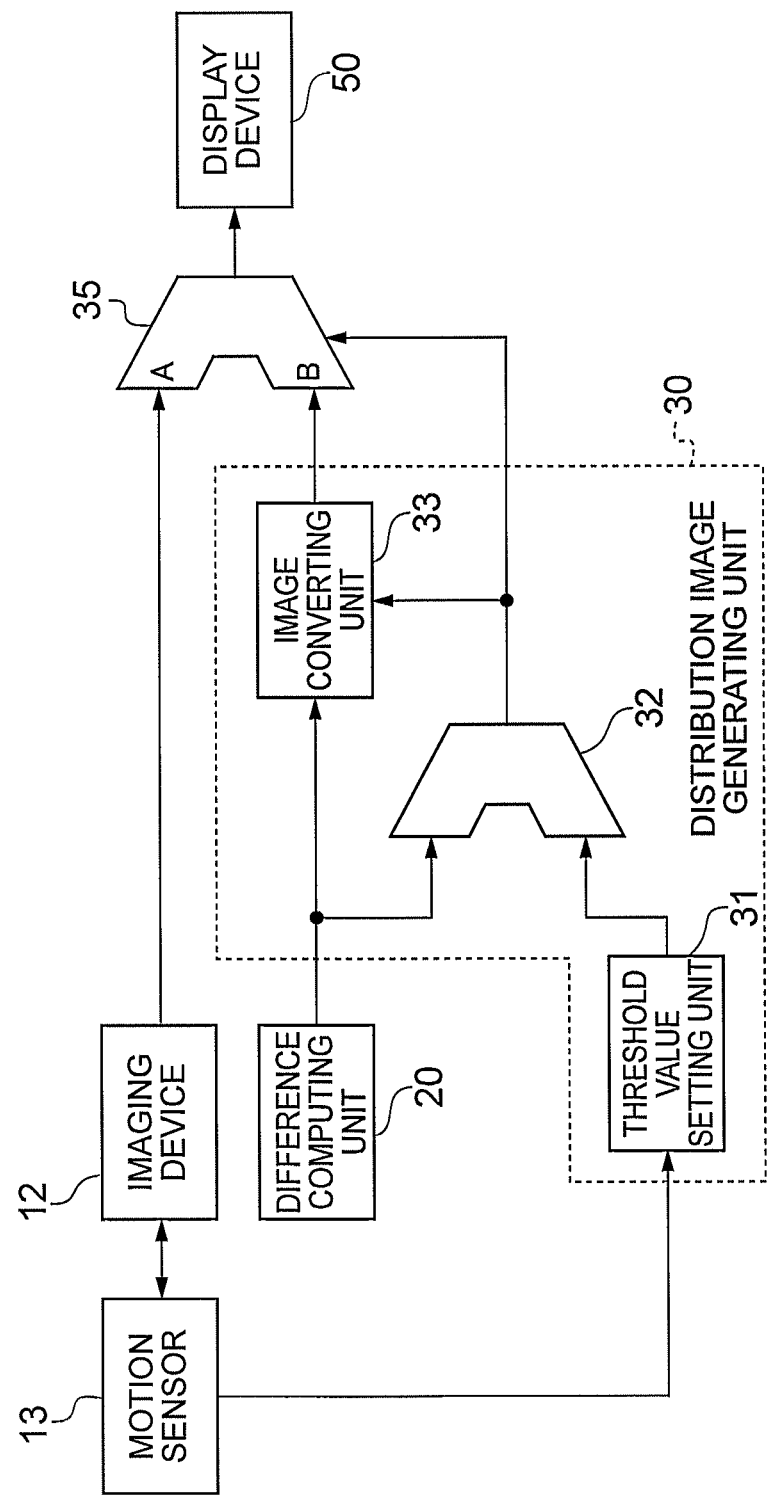

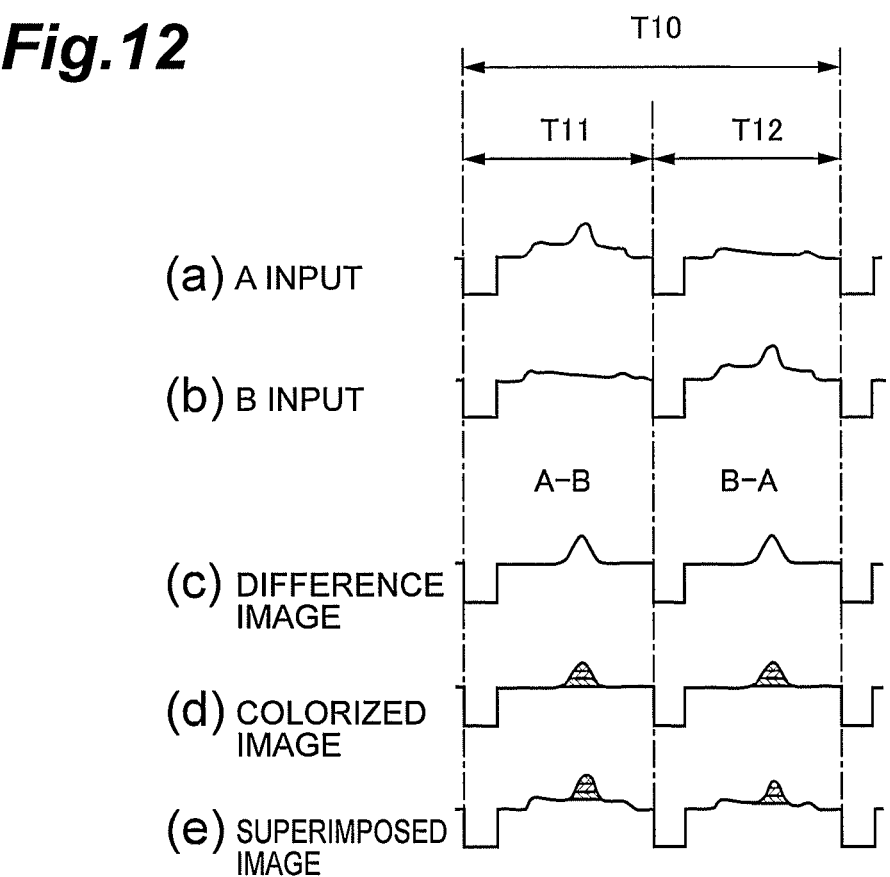

FLUORESCENT LIGHT OBSERVATION DEVICE AND FLUORESCENT LIGHT OBSERVATION METHOD

TECHNICAL FIELD

The present invention relates to a fluorescence observation device and a fluorescence observation method which supply excitation light to an observing object to acquire an observation image of fluorescence from the observing object.

BACKGROUND ART

Fluorescence observation devices which supply and irradiate excitation light at a predetermined wavelength to an observing object to acquire observation images of fluorescence generated from the observing object with an imaging device have been used in, for example, various fields such as the medical field. Further, in a case of observing a temporal change in a state of an object in such fluorescence observation, a method for acquiring images in time series at a predetermined frame rate and observing the object in a moving image is used (refer to, for example, Patent Documents 1 and 2).

CITATION LIST

Patent Literature

Patent Document 1: Japanese Patent Application Laid-Open No. H10-151104
Patent Document 2: Japanese Patent Application Laid-Open No. H7-155292

SUMMARY OF INVENTION

Technical Problem

In observation of fluorescence from an observing object, for the purpose of visually checking an observation image of faint fluorescence, a method for extracting and checking an image component of the fluorescence by generating and displaying a difference image between a fluorescence image acquired in a state in which excitation light is supplied and a background image acquired in a state in which excitation light is not supplied, that is, without fluorescence may be used in some cases. However, in the conventional configuration, in the case where images are acquired sequentially to conduct an observation of the object in a moving image as described above, it is difficult to generate difference images in which fluorescence is extracted in real time in a moving image as it is.

The present invention has been achieved in order to solve the above-described problem, and an object thereof is to provide a fluorescence observation device and a fluorescence observation method which are capable of generating the images in which fluorescence is extracted in real time in a configuration in which observation images of fluorescence from an object are acquired in time series.

Solution to Problem

In order to achieve the above object, a fluorescence observation device according to the present invention includes (1) excitation light supplying means supplying excitation light for fluorescence observation of an observing object and being capable of switching between ON/OFF of the excitation light supply, (2) an interlaced imaging device taking an optical image from the observing object, and alternately outputting first field images and second field images in time series as obtained image data of the observing object, (3) image storage means storing the first field image or the second field image output from the imaging device, and (4) difference image generating means generating a difference image obtained by a difference between one of the first field image and the second field image output from the imaging device, and the other of the first field image and the second field image stored in the image storage means, wherein (5) the excitation light supplying means supplies the excitation light such that one of the first field image acquiring period and the second field image acquiring period by the imaging device is to be a period in which the excitation light supply is turned ON to acquire a fluorescence image, and the other is to be a period in which the excitation light supply is turned OFF to acquire a background image, and (6) the difference image generating means, as its generation mode, switches between a first mode of, in a case where the fluorescence image is output from the imaging device, generating the difference image by subtracting the background image, which is acquired in advance of the fluorescence image to be stored in the image storage means, from the fluorescence image, and a second mode of, in a case where the background image is output from the imaging device, generating the difference image by subtracting the background image from the fluorescence image, which is acquired in advance of the background image to be stored in the image storage means, to apply the mode.

Further, a fluorescence observation method according to the present invention uses a fluorescence observation device including (1) excitation light supplying means supplying excitation light for fluorescence observation of an observing object and being capable of switching between ON/OFF of the excitation light supply, (2) an interlaced imaging device taking an optical image from the observing object, and alternately outputting first field images and second field images in time series as obtained image data of the observing object, and (3) image storage means storing the first field image or the second field image output from the imaging device, wherein the method includes (4) a difference image generating step of generating a difference image obtained by a difference between one of the first field image and the second field image output from the imaging device, and the other of the first field image and the second field image stored in the image storage means, and (5) an excitation light supplying step of supplying the excitation light by the excitation light supplying means such that one of the first field image acquiring period and the second field image acquiring period by the imaging device is to be a period in which the excitation light supply is turned ON to acquire a fluorescence image, and the other is to be a period in which the excitation light supply is turned OFF to acquire a background image, wherein (6) the difference image generating step, as its generation mode, switches between a first mode of, in a case where the fluorescence image is output from the imaging device, generating the difference image by subtracting the background image, which is acquired in advance of the fluorescence image to be stored in the image storage means, from the fluorescence image, and a second mode of, in a case where the background image is output from the imaging device, generating the difference image by subtracting the background image from the fluorescence image, which is acquired in advance of the background image to be stored in the image storage means, to apply the mode.

In the fluorescence observation device and the fluorescence observation method described above, the interlaced imaging device is used for acquisition of fluorescence observation images of the object in time series, and a field image acquiring operation by the imaging device and an ON/OFF operation for excitation light supply by the excitation light supplying means are synchronously controlled such that one of the first field image acquiring period and the second field image acquiring period is to be a fluorescence image acquiring period and the other period is to be a background image acquiring period. At this time, fluorescence images in a state in which excitation light is supplied and background images in a state in which excitation light is not supplied are alternately output in time series as first field images or second field images from the imaging device.

Further, the image storage means is provided as a field memory for the fluorescence image or the background image output in time series from the imaging device. In such a configuration, in a case where a fluorescence image acquired in the fluorescence image acquiring period is output from the imaging device, the image stored in the image storage means is a background image acquired in the previous background image acquiring period. Further, in a case where a background image acquired in the background image acquiring period is output from the imaging device, the image stored in the image storage means is a fluorescence image acquired in the previous fluorescence image acquiring period.

In such a configuration, the difference image generating means for extracting a fluorescence image component in the observation image is provided for the imaging device and the image storage means. Then, in generation of a difference image, the first mode of generating the difference image by subtracting the previous background image of output of the image storage means from the fluorescence image of output of the imaging device, and the second mode of generating the difference image by subtracting the background image of output of the imaging device from the previous fluorescence image of output of the image storage means, are switched to be applied in synchronization with operations of the imaging device and the excitation light supplying means. Accordingly, in the configuration in which fluorescence observation images of the object are acquired in time series, it is possible to generate the images in which fluorescence is extracted in a moving image as it is, in real time without slowing down the image updating rate.

Advantageous Effects of Invention

In accordance with the fluorescence observation device and the fluorescence observation method of the present invention, the field image acquiring operation by the interlaced imaging device and an ON/OFF operation for excitation light supply by the excitation light supplying means are synchronously controlled, and the image storage means is provided for fluorescence images and background images output in time series from the imaging device, and the difference image generating means is provided for the imaging device and the image storage means, and in generation of a difference image, the first mode of generating a difference image by subtracting a background image of output of the image storage means from a fluorescence image of output of the imaging device, and the second mode of generating a difference image by subtracting a background image of output of the imaging device from a fluorescence image of output of the image storage means are switched and applied, thereby it is possible to generate images in which fluorescence is extracted in real time, in the configuration in which fluorescence observation images of the object are acquired in time series.

BRIEF DESCRIPTION OF DRAWINGS

FIG. 5 includes diagrams showing generation of a fake difference image component in a difference image.

FIG. 6 includes diagrams showing removal of the fake difference image component by filter processing.

FIG. 8 includes diagrams showing removal of the fake difference image component by filter processing.

FIG. 10 is a block diagram showing a configuration of a third embodiment of a fluorescence observation device.

FIG. 11 is a block diagram showing an example of a configuration of a distribution image generating unit in the fluorescence observation device shown in FIG. 10.

FIG. 12 is a timing chart showing an example of a fluorescence observation method executed in the fluorescence observation device shown in FIG. 10.

DESCRIPTION OF EMBODIMENTS

Figure 1:
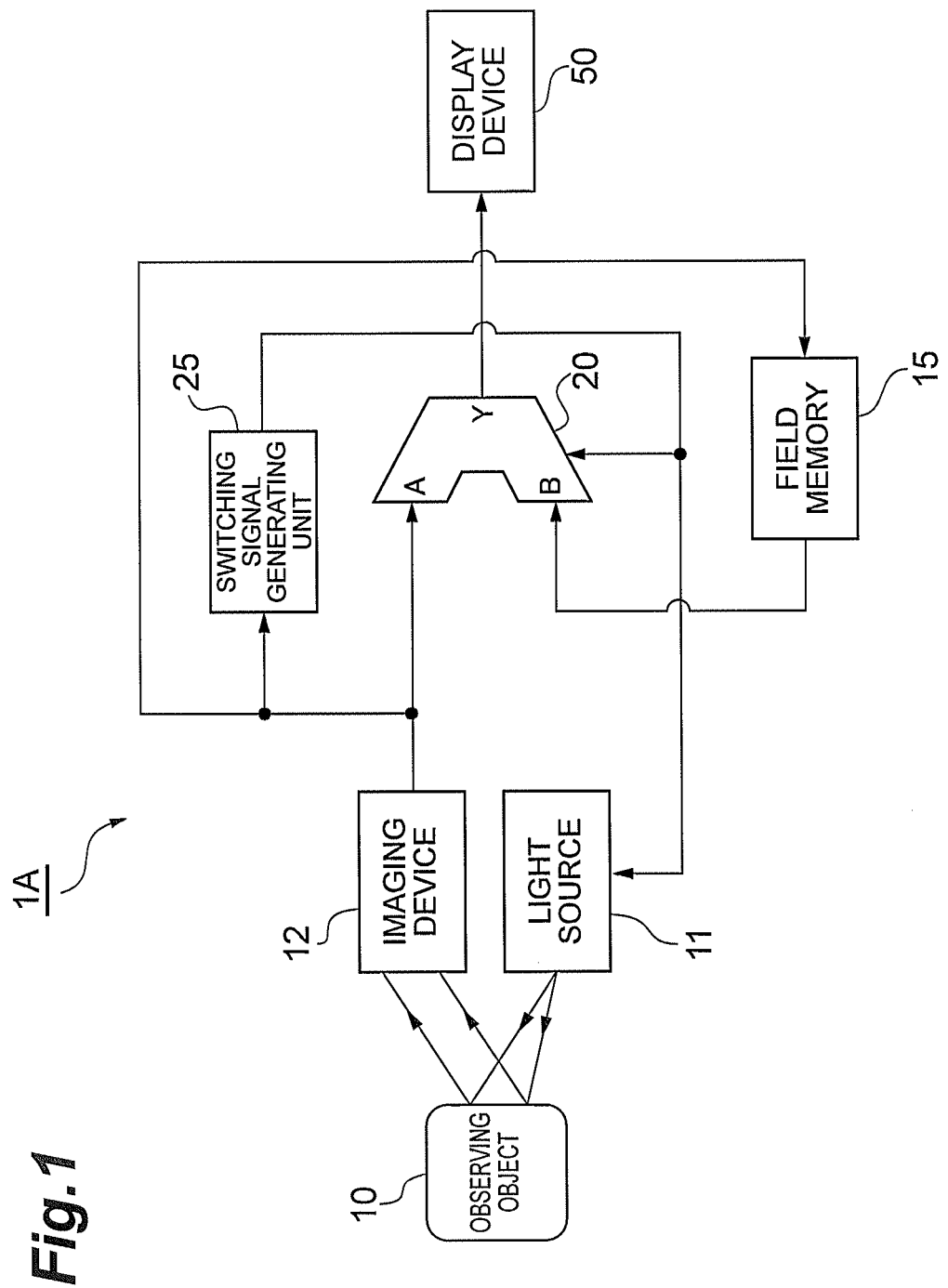
FIG. 1 is a block diagram showing a configuration of a first embodiment of a fluorescence observation device.

Hereinafter, an embodiment of a fluorescence observation device and a fluorescence observation method according to the present invention will be described in detail with reference to the drawings. In the descriptions of the drawings, the same components are denoted by the same reference symbols, and overlapping descriptions will be omitted. In addition, the dimensional ratios in the drawings are not necessarily matched to those in the descriptions.

FIG. 1 is a block diagram showing a configuration of a first embodiment of a fluorescence observation device. A fluorescence observation device 1A according to the present embodiment is configured to observe an object 10 in a moving image by acquiring fluorescence observation images of the observing object 10 in time series at a predetermined frame rate. In detail, the fluorescence observation device 1A includes an observation light source 11, an imaging device 12, a field memory 15, a difference computing unit 20, and a switching signal generating unit 25.

The observation light source 11 is excitation light supplying means which is configured to supply excitation light at a predetermined wavelength for fluorescent observation of the observing object 10, and is capable of switching between ON/OFF of excitation light supply. Further, the imaging device 12 takes an optical image from the object 10, and is an interlaced imaging device that alternately outputs first field images and second field images in time series as image data of the object 10. As such an image device 12, for example, a standard synchronous interlaced video camera with an NTSC system or PAL system may be used.

The observation light source 11 is controlled to operate so as to supply excitation light to the object 10 in synchronization with an operation of the imaging device 12. In detail, the light source 11 supplies excitation light to the object 10 such that, with respect to a first field image acquiring period and a second field image acquiring period by the imaging device 12, one of those periods is to be a fluorescence image acquiring period in which excitation light supply is turned ON to acquire a fluorescence image containing an image component of fluorescence generated in the object 10, and the other period is to be a background image acquiring period in which excitation light supply is turned OFF to acquire a background image without containing an image component of fluorescence (for example, a normal image of the object 10).

In the configuration shown in FIG. 1, in order to realize the above-described synchronization, the switching signal generating unit 25 that generates a switching signal switching in synchronization with the first and second field image acquiring periods based on a signal from the imaging device 12 is provided. Then, the switching signal from the switching signal generating unit 25 is input to the light source 11, thereby realizing synchronous control between the acquisition of first and second field images in the imaging device 12 and ON/OFF of excitation light supply in the light source 11. In such a configuration, with respect to the first and second field images output from the imaging device 12, ones of those are fluorescence images, and the others are background images.

Further, the field memory 15 serving as image storage means for storing the first field image or the second field image (a fluorescence image or a background image) which is output from the imaging device 12 is provided for the imaging device 12. Moreover, the difference computing unit 20 is provided for image output from the imaging device 12 and image output from the field memory 15. The difference computing unit 20 is difference image generating means for generating a difference image obtained by a difference between one of the first and second field images output from the imaging device 12 and the other of the first and second field images stored in the field memory 15 to be output to the computing unit 20.

A switching signal from the switching signal generating unit 25 is input to the difference computing unit 20 in the same way as the observation light source 11. The difference computing unit 20 refers to the input switching signal to switch between a first mode and a second mode which are different in method for generating a difference image to apply the mode as a difference computing generation mode thereof. The first mode is applied in the case where a fluorescence image is output from the imaging device 12, and a difference image is generated by subtracting a background image, which is acquired in advance of the fluorescence image and stored in the field memory 15, from the fluorescence image. Further, the second mode is applied in the case where a background image is output from the imaging device 12, and a difference image is generated by subtracting the background image from a fluorescence image, which is acquired in advance of the background image and stored in the field memory 15.

In the configuration shown in FIG. 1, an arithmetic logic unit (ALU: Arithmetic Logic Unit) is used as the difference computing unit 20. The output (camera output) of the imaging device 12 is connected to the A input terminal of the difference computing unit 20, and the output (memory output) of the field memory 15 is connected to the B input terminal.

Further, a difference image as a computing result is output from the Y output terminal of the difference computing unit 20. In addition, when a computing result is negative in difference computing operation, the result is considered as zero output.

Further, in the configuration example shown in FIG. 1, a display device 50 is connected to the difference computing unit 20, and the configuration is made so as to display a difference image generated in the difference computing unit 20 on the display device 50. However, such a display device 50 may have a configuration in which an image output device other than a display device is provided. Or the configuration may be that an image output device such as a display device is not provided, but data of an acquired difference image are transmitted to the outside.

Figure 2:
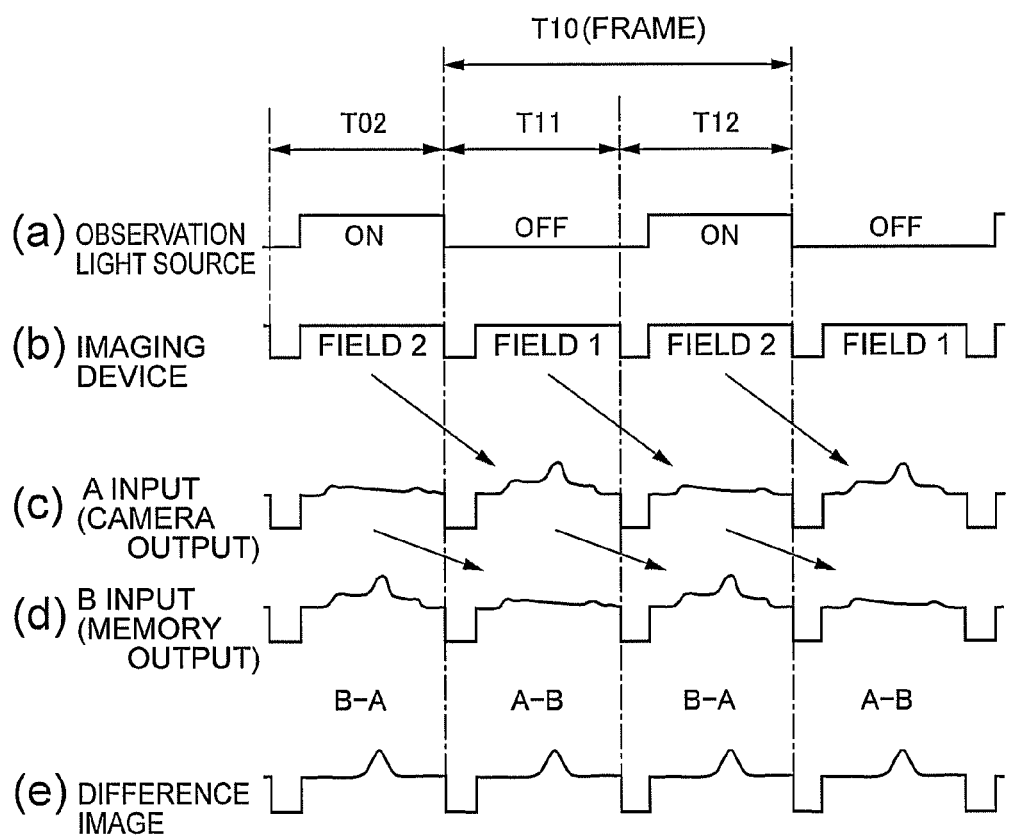
FIG. 2 is a timing chart showing an example of a fluorescence observation method executed in the fluorescence observation device shown in FIG. 1.

FIG. 2 is a timing chart showing an example of a fluorescence observation method executed in the fluorescence observation device shown in FIG. 1. In this timing chart, (a) ON/OFF operations of excitation light supply in the observation light source 11, (b) acquiring operations of first and second field images in the imaging device 12, (c) camera outputs serving as the A input of the difference computing unit 20, (d) memory outputs serving as the B input, and (e) difference images generated by difference computing operation are shown.

In the timing chart of FIG. 2, a frame acquiring period T10 for acquiring an image of one frame is composed of a first period T11 for acquiring a first field image and a second period T12 for acquiring a second field image. Further, in the example of FIG. 2, the supply of excitation light is turned OFF in the first period T11, to set a first field image which is acquired in that period (background image acquiring period) to a background image, and the supply of excitation light is turned ON in the second period T12, to set a second field image which is acquired in that period (fluorescence image acquiring period) to a fluorescence image (excitation light supplying step).

A fluorescence image acquired as a second field image in the imaging device 12 in a second period T02 before the frame acquiring period T10 is output from the imaging device 12 in the following first period T11 to be input to the A input terminal of the difference computing unit 20. Further, in the first period T11, a background image output from the imaging device 12 in the previous second period T02 is stored in the field memory 15, and this background image is input to the B input terminal of the difference computing unit 20 from the field memory 15.

In the first period T11, because the fluorescence image is output from the imaging device 12, the first mode is applied as an operation mode of the difference computing unit 20. At this time, an A−B operation of subtracting the background image of B input from the fluorescence image of A input is executed in the difference computing unit 20, thereby generating a difference image in which fluorescence is extracted (difference image generating step).

Further, the background image acquired as a first field image in the imaging device 12 in the first period T11 of the frame acquiring period T10 is output from the imaging device 12 in the following second period T12 to be input to the A input terminal of the difference computing unit 20. Further, in the second period T12, the fluorescence image output from the imaging device 12 in the previous first period T11 is stored in the field memory 15, and this fluorescence image is input to the B input terminal of the difference computing unit 20 from the field memory 15.

In this second period T12, because the background image is output from the imaging device 12, the second mode is applied as an operation mode of the difference computing unit 20. At this time, a B−A operation of subtracting the background image of A input from the fluorescence image of B input is executed in the difference computing unit 20, thereby generating a difference image in which fluorescence is extracted (difference image generating step).

These excitation light supply from the light source 11, image acquisition in the imaging device 12, switching between the operation modes in the difference computing unit 20, and generation of a difference image are repeatedly carried out in the first periods and the second periods in the respective frame acquiring periods, thereby generating difference images in which fluorescence is extracted in the respective field image acquiring periods. In addition, ON/OFF of excitation light supply in the first and the second periods, acquisition of fluorescence images/background images, and switching between the modes for difference computing operation are not limited to the configuration shown in FIG. 2, and for example, the configuration in which excitation light supply is turned ON in the first period to acquire a fluorescence image, and excitation light supply is turned OFF in the second period to acquire a background image, may be adopted.

Effects of the fluorescence observation device 1A and the fluorescence observation method according to the present embodiment will be described.

In the fluorescence observation device 1A and the fluorescence observation method shown in FIG. 1 and FIG. 2, the interlaced imaging device 12 is used for acquisition of fluorescence observation images of the object 10 in time series, and a field image acquiring operation by the imaging device 12 and an ON/OFF operation for excitation light supply by the observation light source 11 are synchronously controlled such that one of the first field image acquiring period T11 and the second field image acquiring period T12 is to be a fluorescence image acquiring period and the other period is to be a background image acquiring period. At this time, as shown in FIG. 2, fluorescence images in a state in which excitation light is supplied and background images in a state in which excitation light is not supplied are alternately output in time series as first field images or second field images from the imaging device 12.

Further, the field memory 15 is provided for the fluorescence image or the background image output in time series from the imaging device 12. The fluorescence image and the background image output from the imaging device 12 are alternately input in time series as the first field image or the second field image to be stored in this field memory 15. In such a configuration, in the case where a fluorescence image acquired in the fluorescence image acquiring period is output from the imaging device 12, the observation image stored in the field memory 15 is a background image acquired in the previous background image acquiring period. Further, in the case where a background image acquired in the background image acquiring period is output from the imaging device 12, the observation image stored in the field memory 15 is a fluorescence image acquired in the previous fluorescence image acquiring period.

In such a configuration, the difference computing unit 20 for extracting a fluorescence image component in the observation image is provided for the imaging device 12 and the field memory 15. Then, in generation of a difference image, the first mode of generating a difference image by subtracting a previous background image of output of the memory 15 from a fluorescence image of output of the imaging device 12, and the second mode of generating a difference image by subtracting a background image of output of the imaging device 12 from a previous fluorescence image of output of the memory 15 are alternately switched to be applied in synchronization with the operations of the imaging device 12 and the light source 11.

Accordingly, in the configuration of acquiring fluorescence observation images of the object 10 in time series, it is possible to generate the images in which fluorescence is extracted in a moving image as it is in real time without slowing down the image updating rate. For example, in a case where a frame rate of image acquisition is 30 frames per second, a rate of first and second field image acquisition in an interlaced operation is 60 fields per second, that is, twice the frame rate. For this situation, in accordance with the configuration in which a generation mode of a difference image is switched for each field image acquiring period as described above, it is possible to generate and output difference images at 60 images per second, in synchronization with the field image acquiring operation.

Further, in the above-described configuration, the fluorescence observation device 1A uses a configuration in which the switching signal generating unit 25 that generates a switching signal switching in synchronization with a first field image acquiring period and a second field image acquiring period based on a signal from the imaging device 12 is provided, and the difference computing unit 20 switches between the first mode and the second mode based on this switching signal to apply the mode. In this way, by use of a switching signal generated in synchronization with the first and second field image acquiring periods based on a signal from the imaging device 12, it is possible to favorably realize switching of generation mode between the first mode and the second mode in generation of a difference image.

Figure 3:
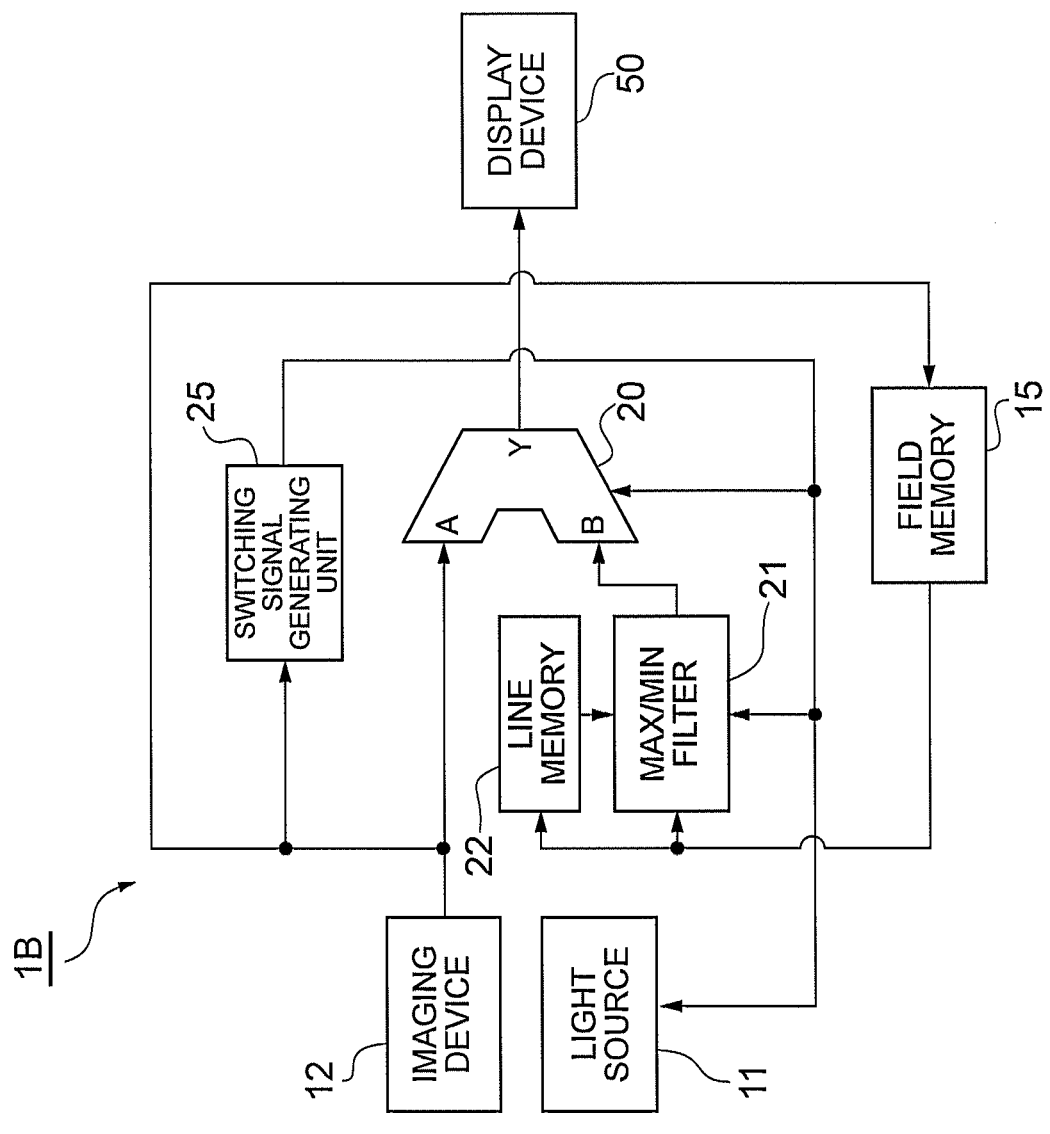
FIG. 3 is a block diagram showing a configuration of a second embodiment of a fluorescence observation device.

FIG. 3 is a block diagram showing a configuration of a second embodiment of a fluorescence observation device. A fluorescence observation device 1B according to the present embodiment includes the observation light source 11, the imaging device 12, the field memory 15, the difference computing unit 20, a MAX/MIN filter 21, a line memory 22, the switching signal generating unit 25, and the display device 50. Among those, the configurations of the observation light source 11, the imaging device 12, the field memory 15, the difference computing unit 20, the switching signal generating unit 25, and the display device 50 are the same as the configurations in the first embodiment shown in FIG. 1. In addition, in FIG. 3, the illustration of the observing object 10 is omitted.

In the configuration shown in FIG. 3, the MAX/MIN filter 21 is provided for a fluorescence image or a background image which is output from the field memory 15 to the difference computing unit 20. This filter 21 is filter processing means for performing maximum filter (MAX filter) processing of setting the maximum intensity at a plurality of pixels including an object pixel and, in addition, pixels within a predetermined range in the vicinity of the object pixel, as the intensity of the object pixel, or minimum filter (MIN filter) processing of setting the minimum intensity at a plurality of pixels including an object pixel and, in addition, pixels within a predetermined range in the vicinity of the object pixel, as the intensity of the object pixel, for the intensities of respective pixels contained in the image, on the image output from the memory 15.

Further, the line memory 22 is provided for this MAX/MIN filter 21. The line memory 22 is second image storage means for storing line image data of scanning lines containing the pixels within the predetermined range in the vicinity of the object pixel, with respect to line image data of the scanning line containing the object pixel in filter processing, and is composed of memories of one line or a plurality of lines according to the contents of filter processing executed in the filter 21. One or a plurality of line image data required for filter processing executed in the filter 21 among the field image data output from the field memory 15 are stored in this line memory 22. Further, with respect to readout of image data from the memory 15 to the filter 21 and the memory 22, in order to get the timing with the image data output from the imaging device 12, early readout of a given amount of data is performed as needed.

In the same way as the light source 11 and the difference computing unit 20, a switching signal from the switching signal generating unit 25 is input to the MAX/MIN filter 21. The filter 21 refers to the input switching signal, to alternately switch between the maximum filter processing and the minimum filter processing, in the first mode in which a background image is output as a processing object in the filter 21 from the field memory 15 and the second mode in which a fluorescence image is output from the field memory 15, so as to synchronize the filter processing with the operations of the imaging device 12, the light source 11, and the difference computing unit 20, to apply the processing. That is, the MAX/MIN filter 21 performs the maximum filter processing on an image from the memory 15 in one of the first and second modes, and performs the minimum filter processing on the image from the memory 15 in the other mode.

Figure 4:
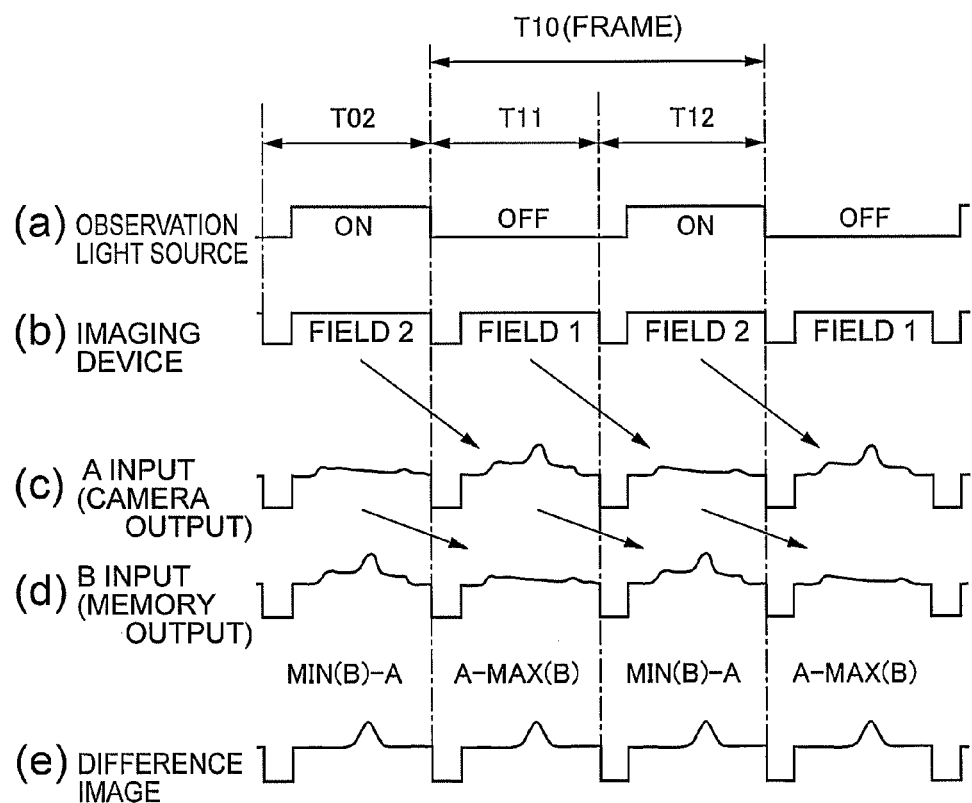
FIG. 4 is a timing chart showing an example of a fluorescence observation method executed in the fluorescence observation device shown in FIG. 3.

FIG. 4 is a timing chart showing an example of a fluorescence observation method executed in the fluorescence observation device shown in FIG. 3. In addition, the basic operations in the timing chart shown in FIG. 4 are the same as those shown in FIG. 2. Further, in the example of FIG. 4, the configuration is adopted such that maximum filter processing is applied to a background image output from the field memory 15 in the first mode, and minimum filter processing is applied to a fluorescence image output from the field memory 15 in the second mode (filter processing step).

The fluorescence image acquired in the imaging device 12 in the second period T02 is input to the A input terminal of the difference computing unit 20 from the imaging device 12 in the first period T11. Further, in the first period T11, the background image output from the imaging device 12 in the previous second period T02 is stored in the memory 15, and this background image is input to the B input terminal of the difference computing unit 20 after the maximum filter processing in the filter 21. In the difference computing unit 20 to which the first mode is applied, an A−MAX(B) operation of subtracting the background image of B input to which the maximum filter processing is applied, from the fluorescence image of A input is executed, thereby generating a difference image in which fluorescence is extracted.

The background image acquired in the imaging device 12 in the first period T11 is input to the A input terminal of the difference computing unit 20 from the imaging device 12 in the second period T12. Further, in the second period T12, the fluorescence image output from the imaging device 12 in the previous first period T11 is stored in the memory 15, and this fluorescence image is input to the B input terminal of the difference computing unit 20 after the minimum filter processing in the filter 21. In the difference computing unit 20 to which the second mode is applied, a MIN(B)−A operation of subtracting the background image of A input, from the fluorescence image of B input to which the minimum filter processing is applied is executed, thereby generating a difference image in which fluorescence is extracted.

Such an excitation light supply from the light source 11, image acquisition in the imaging device 12, switching between the filter processing at the filter 21, switching between the operation modes in the difference computing unit 20, and generation of a difference image are repeatedly carried out in the first periods and the second periods in the respective frame acquiring periods, thereby generating difference images in which fluorescence is extracted in real time in the respective field image acquiring periods.

In the fluorescence observation device 1B and the fluorescence observation method according to the present embodiment as well, the same effects as those in the fluorescence observation device 1A and the fluorescence observation method according to the first embodiment can be obtained. Moreover, in the present embodiment, the configuration is adopted such that the MAX/MIN filter 21 is provided for an image output from the field memory 15 to alternately switch between maximum filter processing and minimum filter processing to be applied to the image in synchronization with switching of the first and second modes in the difference computing unit 20.

As described above, in the configuration in which a field image acquiring operation by the imaging device 12, an excitation light supply operation by the observation light source 11, and a mode switching operation by the difference computing unit 20 are synchronized, because one camera sensor is required, there is no optical position gap between images and it is easy to realize the optical system and mechanism. On the other hand, in such a configuration, a difference is obtained between the different fields of a first field image and a second field image in generation of a difference image, and thus, for example, in some cases, a fake difference image component may be extracted at the boundary between a bright image portion and a dark image portion. Further, such extraction of a fake difference image component may be caused in the same way in the case where there is a movement of the observing object 10, or the like.

In response to this, the MAX/MIN filter 21 which executes maximum filter processing or minimum filter processing for the intensities of the respective pixels in an image output from the field memory 15 is provided, and in this filter 21, the maximum and minimum filter processing are switched in synchronization with a switching operation between the first and second modes in generation of a difference image, to be applied to the image. Thereby, it is possible to suppress extraction of a fake difference image component in a difference image between a fluorescence image and a background image.

In addition, in the case where filter processing is performed on an image serving as the B input of the difference computing unit 20 at the MAX/MIN filter 21, it is necessary for a position of the image of the result of performing the filter processing and a position of a camera image directly input from the imaging device 12 to match to each other. In this case, in readout of image data from the memory 15, it is preferable to perform early readout of data of necessary lines in the vertical direction according to the specific contents of the filter processing.

Further, in the above-described configuration, the fluorescence observation device 1B uses a configuration in which the switching signal generating unit 25 that generates a switching signal switching in synchronization with a first field image acquiring period and a second field image acquiring period based on a signal from the imaging device 12 is provided, and the difference computing unit 20 switches between the first mode and the second mode based on this switching signal to apply the mode, and further, the filter 21 switches between the maximum filter processing and the minimum filter processing in the first mode and the second mode based on the switching signal to apply the processing.

In this way, by use of a switching signal generated in synchronization with the first and second field image acquiring periods based on a signal from the imaging device 12, it is possible to favorably realize switching of generation mode between the first mode and the second mode in generation of a difference image, and switching of filter processing between the maximum filter processing and the minimum filter processing in filter processing.

Further, in the above-described configuration, the line memory 22 which stores line image data of the scanning lines containing pixels within a predetermined range in the vicinity of the object pixel, for line image data of a scanning line containing the object pixel in filter processing is provided in the fluorescence observation device 1B. In such a configuration, by use of the line image data stored in the line memory 22, it is possible to favorably execute filter processing on the image in the filter 21.

With respect to the filter processing executed on an image at the filter 21, the configuration in which, specifically, as the maximum filter processing, with n being an integer of 2 or more, processing of setting the maximum intensity at n pixels, including the object pixel and, in addition, temporally-previous n−1 pixels in the vertical direction which are stored in the line memory 22, as the intensity of the object pixel is performed, and as the minimum filter processing, processing of setting the minimum intensity at n pixels, including the object pixel and, in addition, temporally-previous n−1 pixels in the vertical direction which are stored in the line memory 22, as the intensity of the object pixel is performed, may be used.

In this way, by executing the maximum and minimum filter processing by use of n pixels that temporally-previous n−1 pixels in the vertical direction are added to the object pixel, it is possible to favorably suppress extraction of a fake difference image component. Further, in this case, the number of pixels n used for the maximum filter processing and the minimum filter processing is preferably set to an integer of 3 or more and 5 or less. In addition, the conditions or the like for the maximum and minimum filter processing to be applied to an image will be described later in detail.

Further, with respect to the filter processing, the configuration in which, as the maximum filter processing, with m being an integer of 2 or more, processing of setting the maximum intensity at m pixels, including the object pixel and, in addition, m−1 pixels in the horizontal direction, as the intensity of the object pixel is performed, and as the minimum filter processing, processing of setting the minimum intensity at m pixels, including the object pixel and, in addition, m−1 pixels in the horizontal direction, as the intensity of the object pixel is performed may be used.

In this way, in accordance with the configuration in which the maximum and minimum filter processing are executed by use of m pixels that m−1 pixels in the horizontal direction are added to the object pixel, for example, in the case where there is a movement of the object 10, or the like, it is possible to favorably suppress extraction of a fake difference image component.

The maximum and minimum filter processing executed for a fluorescence image or a background image which is output from the field memory 15 to be the B input of the difference computing unit 20 in the MAX/MIN filter 21, and the effect of suppressing extraction of a fake difference image component thereby will be further described along with the specific examples of the filter processing.

FIG. 5 is a figure including diagrams showing generation of fake difference image components in a difference image between a fluorescence image and a background image. Here, as shown in (a) in FIG. 5, a case where there is a rectangular bright image portion 61 in its central portion, and there is a dark image portion 62 circumferentially in an observation image 60 will be considered. In addition, in the following respective drawings, the solid lines show scanning lines of a field image which is input to the A input terminal of the difference computing unit 20, and the dashed lines show scanning lines of a field image which is input to the B input terminal of the difference computing unit 20. Further, in (a) in FIG. 5, the illustration of scanning lines in the bright image portion 61 is omitted.

In (b) in FIG. 5, P shows an intensity distribution along the line P in the vertical direction shown in (a) in FIG. 5. In this intensity distribution P, at the top edge 66 of the bright image portion 61, with respect to the A input scanning line A1 and the B input scanning line B1 to be objects of difference computing operation, while the intensity on the scanning line A1 is "dark", the intensity on the scanning line B1 is "bright". At this time, a fake difference image component C1 is generated in a difference image by a B−A operation. In the same way, at the bottom edge 67 of the bright image portion 61, while the intensity on the scanning line A2 is "bright", the intensity on the scanning line B2 is "dark". At this time, a fake difference image component C2 is generated in a difference image by an A−B operation.

For such fake difference image components, as shown in FIG. 6, it is possible to remove the fake difference image components by filter processing. Here, in FIG. 6, the number of pixels for filter processing is set to n=2, and the maximum filter processing is served as processing of setting the maximum intensity at 2 pixels, including a temporally-previous one pixel in the vertical direction in addition to an object pixel, as the intensity of the object pixel. In the same way, the minimum filter processing is served as processing of setting the minimum intensity at 2 pixels, including a temporally-previous one pixel in the vertical direction in addition to an object pixel, as the intensity of the object pixel.

(a) in FIG. 6 shows the minimum filter (MIN filter) processing to be applied to generation of a fake image component by a B−A operation at the top edge 66 of the bright image portion 61. In this case, the intensity on the scanning line B1 is "bright" in the original intensity distribution P, however, as a result of executing the MIN filter processing on the image of B input, in the obtained intensity distribution MIN(B), the intensity on the scanning line one level above the scanning line B1 (the temporally-previous scanning line in the vertical direction) is "dark", and therefore, the intensity on the scanning line B1 is replaced with "dark". Accordingly, a fake image component is no longer generated in a difference image by a MIN(B)−A operation. This corresponds to the case where the image of B input is a fluorescence image (refer to FIG. 4).

(b) in FIG. 6 shows the maximum filter (MAX filter) processing to be applied to generation of a fake image component by an A−B operation at the bottom edge 67 of the bright image portion 61. In this case, the intensity on the scanning line B2 is "dark" in the original intensity distribution P, however, as a result of executing the MAX filter processing on the image of B input, in the obtained intensity distribution MAX(B), the intensity on the scanning line one level above the scanning line B2 is "bright", and therefore, the intensity on the scanning line B2 is replaced with "bright". Accordingly, a fake image component is no longer generated in a difference image by an A−MAX(B) operation. This corresponds to the case where the image of B input is a background image.

Here, in FIG. 6, there has been described the case where, the number of pixels for filter processing is set to n=2, and the maximum and minimum filter processing are performed by use of 2 pixels that a temporally-previous one pixel in the vertical direction is added to an object pixel, as described above. However, in an actual natural image, in some cases, the removal performance for a fake difference image component may be poor in such filter processing.

Figure 7:
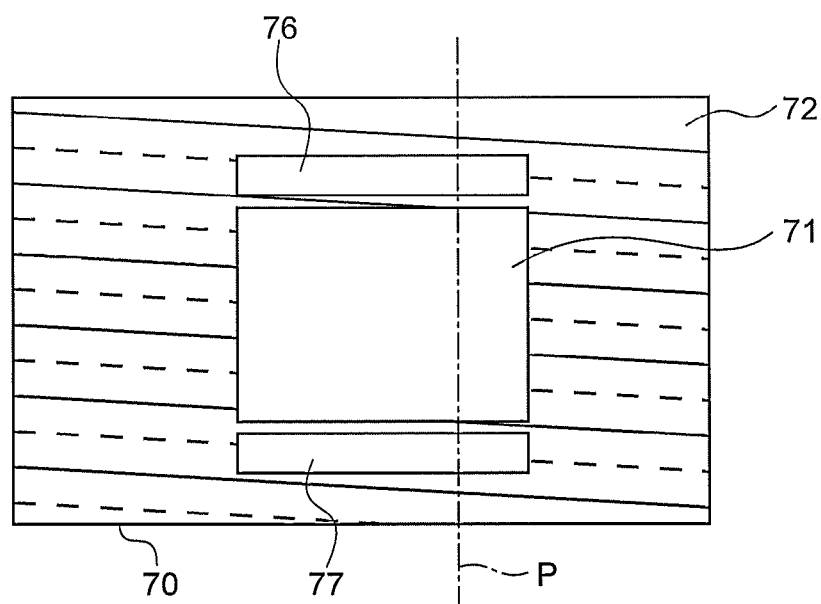
FIG. 7 is a diagram showing generation of a fake difference image component in a difference image.

FIG. 7 is a diagram showing another example of generation of fake difference image components in a difference image between a fluorescence image and a background image. Here, a case where there is a rectangular bright image portion 71 in its central portion, and there is a dark image portion 72 circumferentially, and moreover, there are respectively bright image portions 76 and 77 in the vicinity of the upper and lower edges of the image portion 71 in an observation image 70, will be considered. In the case where there is a fluctuation in intensity distribution including the image portions 76 and 77 at the boundary between the bright image portion 71 and the dark image portion 72 in a natural image, even if the maximum and minimum filter processing are performed as described above, a fake image component may be generated.

(a) and (b) in FIG. 8 respectively show the minimum filter (MIN filter) processing to be applied to generation of fake image components by a B−A operation in the bright image portion 71 and the bright image portion 76 above the image portion 71. In (a) in FIG. 8, the number of pixels for filter processing is set to n=2 in the same way as in FIG. 6, and the minimum filter processing is served as processing of setting the minimum intensity at 2 pixels, including a temporally-previous one pixel in the vertical direction in addition to an object pixel, as the intensity of the object pixel. Further, in (b) in FIG. 8, the number of pixels for filter processing is set to n=3, and the minimum filter processing is served as processing of setting the minimum intensity at 3 pixels, including temporally-previous two pixels in the vertical direction in addition to an object pixel, as the intensity of the object pixel.

In (a) in FIG. 8, in the original intensity distribution P, while the intensity on the scanning line A1 is "dark", the intensity on the scanning line B1 is "bright", and the intensity on the scanning line B6 one level above the scanning line B1 is "bright" in the same way. In this case, even when the MIN filter processing with n=2 is executed on the image of B input, the intensity on the scanning line B1 stays "bright" in the obtained intensity distribution MIN(B), and accordingly, a fake image component C1 is generated in a difference image by a MIN(B)−A operation.

On the other hand, as shown in (b) in FIG. 8, for the same intensity distribution P, in the case where the MIN filter processing with n=3 is executed on the image of B input, the intensity on the scanning line B7 two levels above the scanning line B1 is "dark", and therefore, the intensity on the scanning line B1 is replaced with "dark" in the obtained intensity distribution MIN(B). Accordingly, a fake image component is no longer generated in a difference image by a MIN(B)−A operation. In addition, it is possible to execute such removal of a fake image component for a fake image component by an A−B operation in the same way.

In this way, in the maximum and minimum filter processing in the vertical direction, in the case where the number of pixels n in the vicinity of an object pixel to which the filter processing is applied is set to a larger number, it is possible to improve the removal performance for a fake difference image component thereby. On the other hand, when the number of pixels n is increased, problems such as expansion in circuit scale for executing the filter processing are caused. Further, execution of filter processing with the larger number of pixels n has an effect of, for example, reducing the size of a difference image itself, and deforms an extracted target image as well, and therefore, the number of pixels n should not be increased more than necessary.

In view of such a point, the number of pixels n in the vicinity of the object pixel, which is used for the maximum and minimum processing, is preferably set to an integer of 3 or more and 5 or less ($3 \leq n \leq 5$) as described above. Further, the configuration in which temporally-subsequent pixels in the vertical direction with respect to an object pixel as well are used for filter processing according to the filter processing circuit, the memory configuration, and the like, may be adopted.

Further, generation of a fake difference image component in a difference image between a fluorescence image and a background image may occur, for example, in a case where there is a movement at a speed faster than or equal to a field time in the observing object 10, other than at the boundary between the bright image portion and the dark image portion described above. In a case of a fake image component due to a movement of the object 10, it is possible to remove the movement in the vertical direction by the filter processing by use of n pixels in the vertical direction described above.

Further, it is possible to remove fake image components due to the movement in the horizontal direction by performing the similar filter processing by use of m pixels including m−1 pixels in the horizontal direction in addition to an object pixel. In this case, the number of pixels m used for the maximum and minimum filter processing in the horizontal direction is, in view of the same point as in the case of the vertical direction, preferably set to an integer of 5 or more and 7 or less ($5 \leq m \leq 7$). Further, in the case where the filter processing is performed both in the horizontal direction and the vertical direction, for example, the filter processing may be performed by use of n×m pixels including an object pixel.

In addition, in the timing chart shown in FIG. 4, ON/OFF of excitation light supply in the first and second periods, acquisition of fluorescence images/background images, switching between the operation modes for a difference computing operation, and execution of the filter processing are not limited to the configuration shown in FIG. 4 as described with respect to FIG. 2, and for example, the configuration in which excitation light supply is turned ON in the first period to acquire a fluorescence image, and excitation light supply is turned OFF in the second period to acquire a background image, may be adopted.

Figure 9:
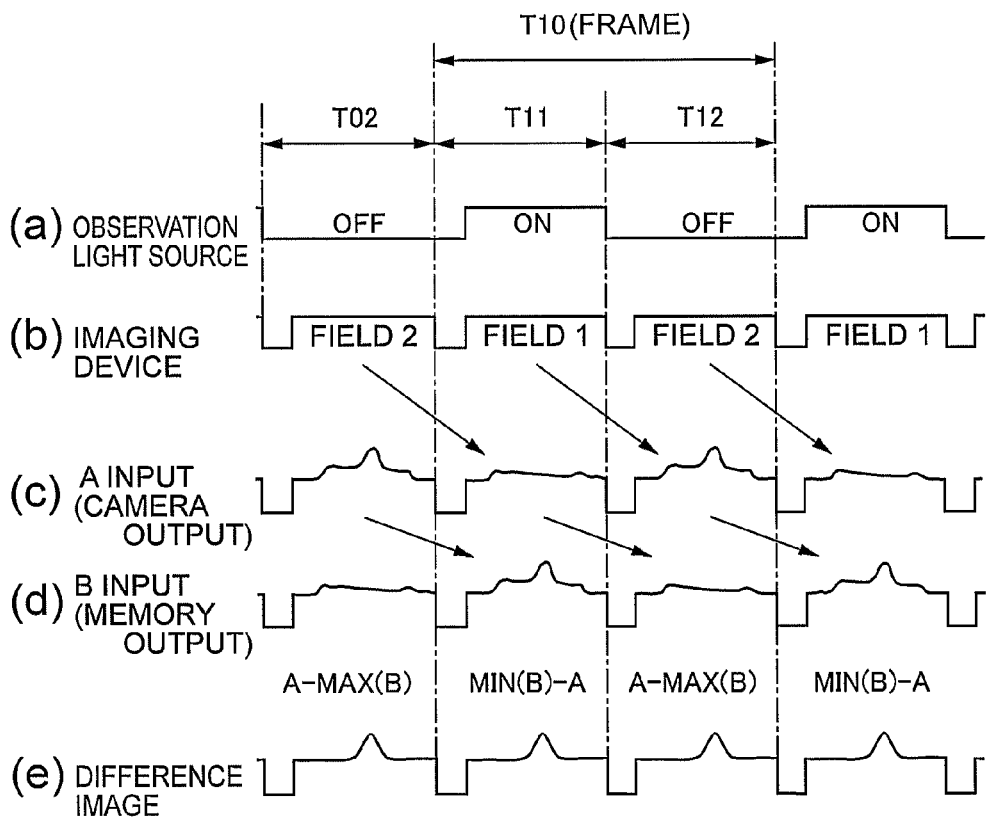
FIG. 9 is a timing chart showing another example of a fluorescence observation method executed in the fluorescence observation device shown in FIG. 3.

FIG. 9 is a timing chart showing another example of a fluorescence observation method executed in the fluorescence observation device shown in FIG. 3. In this example of FIG. 9, in contrast to the example of FIG. 4, the supply of excitation light is turned ON in the first period T11, and a first field image acquired in the period is a fluorescence image, and the supply of excitation light is turned OFF in the second period T12, and a second field image acquired in the period is a background image.

The background image acquired in the imaging device 12 in the second period T02 is input to the A input terminal of the difference computing unit 20 from the imaging device 12 in the first period T11. Further, in the first period T11, the fluorescence image output from the imaging device 12 in the previous second period T02 is stored in the memory 15, and this fluorescence image is input to the B input terminal of the difference computing unit 20 after the minimum filter processing in the filter 21. In the difference computing unit 20 to which the second mode is applied, a MIN(B)−A operation of subtracting the background image of A input from the fluorescence image of B input to which the minimum filter processing is applied is executed, thereby generating a difference image in which fluorescence is extracted.

The fluorescence image acquired in the imaging device 12 in the first period T11 is input to the A input terminal of the difference computing unit 20 from the imaging device 12 in the second period T12. Further, in the second period T12, the background image output from the imaging device 12 in the previous first period T11 is stored in the memory 15, and this background image is input to the B input terminal of the difference computing unit 20 after the maximum filter processing in the filter 21. In the difference computing unit 20 to which the first mode is applied, an A−MAX(B) operation of subtracting the background image of B input to which the maximum filter processing is applied from the fluorescence image of A input is executed, thereby generating a difference image in which fluorescence is extracted.

These excitation light supply from the light source 11, image acquisition in the imaging device 12, switching between the filter processing at the filter 21, switching between the operation modes in the difference computing unit 20, and generation of a difference image are repeatedly carried out in the first periods and the second periods in the respective frame acquiring periods, thereby, in the same way as in the case of FIG. 4, generating difference images in which fluorescence is extracted in real time in the respective field image acquiring periods.

FIG. 10 is a block diagram showing a configuration of a third embodiment of a fluorescence observation device. A fluorescence observation device 1C according to the present embodiment includes the observation light source 11, the imaging device 12, the field memory 15, the difference computing unit 20, the MAX/MIN filter 21, the line memory 22, the switching signal generating unit 25, a distribution image generating unit 30, a multiplexer 35, and the display device 50. Among those, the configurations of the observation light source 11, the imaging device 12, the field memory 15, the difference computing unit 20, the MAX/MIN filter 21, the line memory 22, the switching signal generating unit 25, and the display device 50 are the same as the configurations in the second embodiment shown in FIG. 3.

In the configuration shown in FIG. 10, the distribution image generating unit 30 is provided for a difference image between a fluorescence image and a background image which is output from the difference computing unit 20. This distribution image generating unit 30 is distribution image generating means for generating an intensity distribution image showing fluorescence intensity distribution based on the difference image output from the difference computing unit 20. As an intensity distribution image in this case, specifically, for example, the configuration in which a single or a plurality of threshold values are applied to the difference image to generate a binarized image or a colorized image serving as the intensity distribution image may be used.

Further, the multiplexer 35 is provided for an output from the imaging device 12, and an output from the distribution image generating unit 30. This multiplexer 35 is superimposed image generating means for generating a superimposed image in which the fluorescence image or the background image output from the imaging device 12 and the fluorescence intensity distribution image output from the distribution image generating unit 30 are superimposed.

In the configuration of FIG. 10, the output of the imaging device 12 is connected to the A input terminal of the multiplexer 35, and the output of the distribution image generating unit 30 is connected to the B input terminal. Further, a superimposition instruction signal from the distribution image generating unit 30 is input to the multiplexer 35, and superimposed image of an image input from the imaging device 12 and an image input from the distribution image generating unit 30 is generated with reference to the contents of instruction by this superimposition instruction signal. Further, the superimposed image generated in the multiplexer 35 is output to the display device 50.

FIG. 11 is a block diagram showing an example of a configuration of the distribution image generating unit in the fluorescence observation device 1C shown in FIG. 10. The distribution image generating unit 30 in the present configuration example has a threshold value setting unit 31, a comparator 32, and an image converting unit 33, that is configured to apply a plurality of (N) threshold values to a difference image input from the difference computing unit 20 to generate a colorized image (false colorized image) corresponding to the fluorescence intensity distribution.

The threshold value setting unit 31 includes a CPU for example, and sets N threshold values for generating a colorized image showing the fluorescence intensity distribution. Further, in the configuration example of FIG. 11, a 3 G motion sensor 13 is provided for the imaging device 12, and the threshold value setting unit 31 sets and changes threshold values with reference to information on a movement of the imaging device 12 detected by the sensor 13. Such a configuration has a beneficial effect, for example, in the case where a camera shake in the imaging device 12 is detected, and threshold values used for extraction of a difference image component are dynamically increased based on the amount of the shake to obscure a fake difference image component, or the like. In addition, because a camera shake in the imaging device 12 is a movement with the camera support point, the movement of the image may increase in many cases, it is impossible to completely remove the movement with only a spatial filter method by the maximum and minimum filter processing described above in some cases.

The comparator 32 is an N-step comparator which compares the N threshold values set in the threshold value setting unit 31 and the intensities of the respective pixels in a difference image input from the difference computing unit 20 to output determined values in N-steps as the comparison results thereof. Further, the image converting unit 33 converts the difference image from the difference computing unit 20 into a false colorized difference image in N-colors based on an N-value switching signal indicating the determined values in N-steps output from the comparator 32. In addition, for pixels of intensity lower than the N threshold values, it is considered that fluorescence is not generated so that colorized image data is not generated.

In such a configuration, an original image (a fluorescence image or a background image) from the imaging device 12, a false colorized difference image showing the fluorescence intensity distribution from the image converting unit 33, and an N-value switching signal (a superimposition instruction signal) from the comparator 32 are input to the multiplexer 35. The multiplexer 35 refers to the N-value switching signal to perform switching between image data in units of pixels so as to adopt original image data from the imaging device 12 for pixels whose colorized images are not generated, and adopt colorized image data from the image converting unit 33 for pixels whose colorized images are generated, thereby generating a superimposed image of the original image and the colorized difference image (intensity distribution image). In addition, in such a configuration, if the number of threshold values is N=1, a binarized image is generated as an intensity distribution image.

FIG. 12 is a timing chart showing an example of a fluorescence observation method executed in the fluorescence observation device shown in FIG. 10. In this timing chart, (a) camera outputs serving as the A input of the difference computing unit 20, (b) memory outputs serving as the B input, (c) difference images generated in the difference computing unit 20, (d) colorized images generated in the distribution image generating unit 30, and (e) superimposed images generated in the multiplexer 35 are shown.

In addition, the basic operations in the timing chart shown in FIG. 12 are the same as those shown in FIG. 2 other than the generation of a colorized image and the generation of a superimposed image. Further, in FIG. 12, the illustrations of the maximum and minimum filter processing executed at the MAX/MIN filter 21 are omitted.

In the first period T11, a difference image is generated by an A–B operation of subtracting the background image of B input from the fluorescence image of A input in the difference computing unit 20. Further, in the distribution image generating unit 30, a colorized difference image in N colors showing the fluorescence intensity distribution is generated by applying N threshold values to the difference image (distribution image generating step). Moreover, in the multiplexer 35, a superimposed image of the colorized difference image output from the generating unit 30 and the fluorescence image output from the imaging device 12 is generated (superimposed image generating step).

In the same way, in the second period T12, a difference image is generated by a B–A operation of subtracting the background image of A input from the fluorescence image of B input in the difference computing unit 20. Further, in the distribution image generating unit 30, a colorized difference image in N colors is generated by applying N threshold values to the difference image (distribution image generating step). Moreover, in the multiplexer 35, a superimposed image of the colorized difference image output from the generating unit 30 and the background image output from the imaging device 12 is generated (superimposed image generating step).

In the fluorescence observation device 1C and the fluorescence observation method according to the present embodiment as well, the same effects as those in the fluorescence observation device 1A according to the first embodiment and the fluorescence observation device 1B according to the second embodiment can be obtained.

Moreover, in the present embodiment, the configuration is adopted such that the distribution image generating unit 30 is provided for a difference image output from the difference computing unit 20 to generate an intensity distribution image such as a binarized image or a colorized image showing the fluorescence intensity distribution based on the difference image. In this way, the difference image in which fluorescence is extracted is not directly used, but is converted into an intensity distribution image in the distribution image generating unit 30 to be used for fluorescence observation, thereby, it is possible to efficiently carry out various operations such as visual check of an observation image of faint fluorescence.

Further, in the present embodiment, the configuration in which the multiplexer 35 which generates a superimposed image of an original image output from the imaging device 12 and an intensity distribution image output from the distribution image generating unit 30 is provided, is adopted. In this way, in accordance with the configuration in which a superimposed image of an original fluorescence image or background image and an intensity distribution image processed by applying threshold values thereto is used for fluorescence observation, for example, efficient fluorescence observation of the object is possible in various manners, such as visually checking a generating position of fluorescence in the object 10 from an observation image displayed on the display device 50.

Figure 13A:
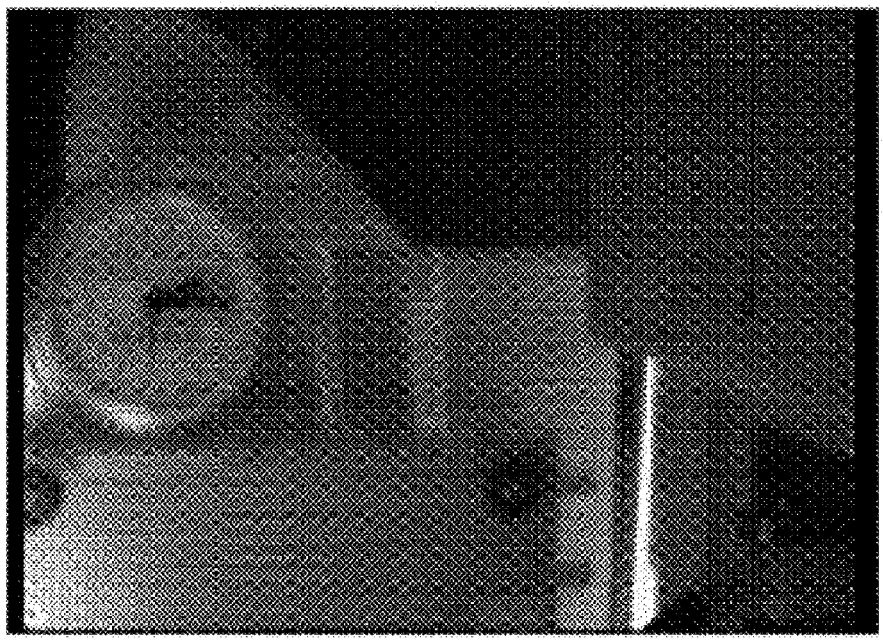
FIG. 13(A) shows a normal observation image acquired in the fluorescence observation device.
Figure 13B:
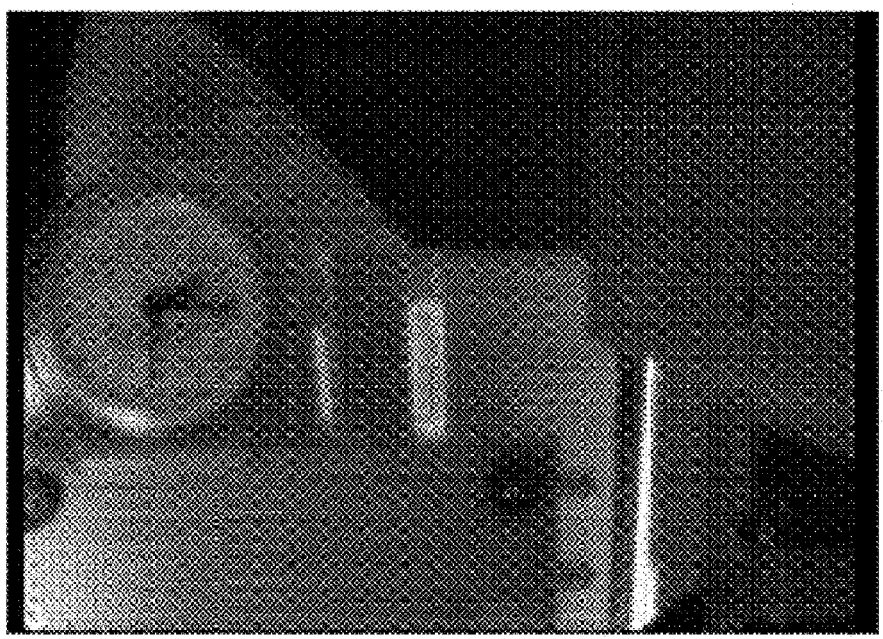
FIG. 13(B) shows a superimposed image in which a false colorized difference image is superimposed on the original image.

Here, FIG. 13 is a figure including diagrams showing examples of observation images acquired in the fluorescence observation device 1C shown in FIG. 10. (a) in FIG. 13 shows a normal observation image to which fluorescence extraction by generation of a colorized image and generation of a superimposed image are not carried out, and (b) in FIG. 13 shows a superimposed image in which a false colorized difference image is superimposed on the original image. In this way, by generating and displaying an intensity distribution image such as a colorized image showing the fluorescence intensity distribution, or moreover, a superimposed image of an original image and an intensity distribution image, it is possible to favorably check a generating position, a range, and the intensity distribution of fluorescence in an observing object.

The fluorescence observation device and the fluorescence observation method according to the present invention are not limited to the above-described embodiments and the configuration examples, and various modifications are possible. For example, the configurations of the difference image generating means, the filter processing means, the distribution image generating means, and the superimposed image generating means and the like are not limited to the configurations of the above-described embodiments, and specifically, various configurations may be used. Further, for example, the distribution image generating unit 30 and the multiplexer 35 shown in FIG. 10 may be applied to the configuration in which the MAX/MIN filter 21 is not provided as in FIG. 1. Further, the configuration in which the multiplexer 35 which generates a superimposed image is not provided, and an intensity distribution image generated in the distribution image generating unit 30 is directly displayed on the display device 50, may be adopted.

The fluorescence observation device according to the above-described embodiment includes (1) excitation light supplying means for supplying excitation light for fluorescence observation of an observing object and being capable of switching between ON/OFF of the excitation light supply, (2) an interlaced imaging device for taking an optical image from the observing object, and alternately outputting first field images and second field images in time series as obtained image data of the observing object, (3) image storage means for storing the first field image or the second field image output from the imaging device, and (4) difference image generating means for generating a difference image obtained by a difference between one of the first field image and the second field image output from the imaging device, and the other of the first field image and the second field image stored in the image storage means, the device uses a configuration in which (5) the excitation light supplying means supplies the excitation light such that one of the first field image acquiring period and the second field image acquiring period by the imaging device is to be a period in which the excitation light supply is turned ON to acquire a fluorescence image, and the other is to be a period in which the excitation light supply is turned OFF to acquire a background image, and (6) the difference image generating means, as its generation mode, switches between a first mode of, in a case where the fluorescence image is output from the imaging device, generating the difference image by subtracting the background image, which is acquired in advance of the fluorescence image and stored in the image storage means, from the fluorescence image, and a second mode of, in a case where the background image is output from the imaging device, generating the difference image by subtracting the background image from the fluorescence image, which is acquired in advance of the background image and stored in the image storage means, to apply the mode.

Further, the fluorescence observation method according to the above-described embodiment which uses a fluorescence observation device including (1) excitation light supplying means for supplying excitation light for fluorescence observation of an observing object and being capable of switching between ON/OFF of the excitation light supply, (2) an interlaced imaging device for taking an optical image from the observing object, and alternately outputting first field images and second field images in time series as obtained image data of the observing object, and (3) image storage means for storing the first field image or the second field image output from the imaging device, the method includes (4) a difference image generating step of generating a difference image obtained by a difference between one of the first field image and the second field image output from the imaging device, and the other of the first field image and the second field image stored in the image storage means, and (5) an excitation light supplying step of supplying the excitation light by the excitation light supplying means such that one of the first field image acquiring period and the second field image acquiring period by the imaging device is to be a period in which the excitation light supply is turned ON to acquire a fluorescence image, and the other is to be a period in which the excitation light supply is turned OFF to acquire a background image, the method uses a configuration in which (6) the difference image generating step, as its generation mode, switches between a first mode of, in a case where the fluorescence image is output from the imaging device, generating the difference image by subtracting the background image, which is acquired in advance of the fluorescence image and stored in the image storage means, from the fluorescence image, and a second mode of, in a case where the background image is output from the imaging device, generating the difference image by subtracting the background image from the fluorescence image, which is acquired in advance of the background image and stored in the image storage means, to apply the mode.

Here, the fluorescence observation device may use a configuration which includes switching signal generating means for generating a switching signal switching in synchronization with the first field image acquiring period and the second field image acquiring period based on a signal from the imaging device, and the difference image generating means switches between the first mode and the second mode based on the switching signal to apply the mode. In the same way, the fluorescence observation method may use a configuration which includes a switching signal generating step of generating a switching signal switching in synchronization with the first field image acquiring period and the second field image acquiring period based on a signal from the imaging device, and the difference image generating step switches between the first mode and the second mode based on the switching signal to apply the mode.

In this way, by use of a switching signal generated in synchronization with the first and second field image acquiring periods based on a signal from the imaging device, it is possible to favorably realize switching of generation mode between the first mode and the second mode in generation of a difference image.

Further, it is preferable that the fluorescence observation device includes filter processing means for performing, for the intensities of respective pixels contained in the image which is the fluorescence image or the background image output from the image storage means to the difference image generating means, maximum filter processing of setting the maximum intensity at a plurality of pixels, including pixels within a predetermined range in the vicinity of an object pixel in addition to the object pixel, as the intensity of the object pixel, or minimum filter processing of setting the minimum intensity at a plurality of pixels, including pixels within a predetermined range in the vicinity of an object pixel in addition to the object pixel, as the intensity of the object pixel, and the filter processing means switches between the maximum filter processing and the minimum filter processing in the first mode in which the background image is output from the image storage means, and in the second mode in which the fluorescence image is output from the image storage means, to apply the processing.

In the same way, it is preferable that the fluorescence observation method includes a filter processing step of performing, for the intensities of respective pixels contained in the image which is the fluorescence image or the background image output from the image storage means, maximum filter processing of setting the maximum intensity at a plurality of pixels, including pixels within a predetermined range in the vicinity of an object pixel in addition to the object pixel, as the intensity of the object pixel, or minimum filter processing of setting the minimum intensity at a plurality of pixels, including pixels within a predetermined range in the vicinity of an object pixel in addition to the object pixel, as the intensity of the object pixel, and the filter processing step switches between the maximum filter processing and the minimum filter processing in the first mode in which the background image is output from the image storage means, and in the second mode in which the fluorescence image is output from the image storage means, to apply the processing.

As described above, in the configuration in which a field image acquiring operation by the imaging device, an excitation light supply operation by the excitation light supplying means, a mode switching operation by the difference image generating means are synchronized, because a difference is obtained between a first field image and a second field image in generation of a difference image, a fake difference image component may be extracted, for example, at the boundary between a bright image portion and a dark image portion in some cases. Further, such extraction of a fake difference image component may be caused in the case where there is a movement of the object, or the like.

In response to this, the filter processing means for executing the maximum filter processing or the minimum filter processing for the intensities of the respective pixels in the image output from the image storage means is provided, and in this filter processing means, the maximum and minimum filter processing are switched in synchronization with a switching operation between the first and second modes in generation of a difference image, to be applied to the image. Thereby, it is possible to suppress extraction of a fake difference image component in a difference image between a fluorescence image and a background image.

In this case, the fluorescence observation device may use a configuration which includes switching signal generating means for generating a switching signal switching in synchronization with the first field image acquiring period and the second field image acquiring period based on a signal from the imaging device, and the difference image generating means switches between the first mode and the second mode based on the switching signal to apply the mode, and the filter processing means switches between the maximum filter processing and the minimum filter processing in the first mode and the second mode based on the switching signal to apply the processing.

In the same way, the fluorescence observation method may use a configuration which includes a switching signal generating step of generating a switching signal switching in synchronization with the first field image acquiring period and the second field image acquiring period based on a signal from the imaging device, and the difference image generating step switches between the first mode and the second mode based on the switching signal to apply the mode, and the filter processing step switches between the maximum filter processing and the minimum filter processing in the first mode and the second mode based on the switching signal to apply the processing.

In this way, by use of a switching signal generated in synchronization with the first and second field image acquiring periods based on a signal from the imaging device, it is possible to favorably realize switching of generation mode between the first mode and the second mode in generation of a difference image and switching of filter processing between the maximum filter processing and the minimum filter processing in filter processing.

Further, in the case of using the filter processing means as described above, the fluorescence observation device preferably includes second image storage means for storing line image data of scanning lines containing the pixels within the predetermined range in the vicinity of the object pixel, with respect to line image data of a scanning line containing the object pixel. In accordance with such a configuration, by use of the line image data stored in the second image storage means, it is possible to favorably execute filter processing for an image by the filter processing means.

With respect to the filter processing on a fluorescence image or a background image, specifically, the fluorescence observation device may use a configuration in which, in the filter processing means, as the maximum filter processing, with n being an integer of 2 or more, processing of setting the maximum intensity at n pixels, including temporally-previous n−1 pixels in the vertical direction in addition to the object pixel, as the intensity of the object pixel is performed, and as the minimum filter processing, processing of setting the minimum intensity at n pixels, including temporally-previous n−1 pixels in the vertical direction in addition to the object pixel, as the intensity of the object pixel is performed.

In the same way, the fluorescence observation method may use a configuration in which, in the filter processing step, as the maximum filter processing, with n being an integer of 2 or more, processing of setting the maximum intensity at n pixels, including temporally-previous n−1 pixels in the vertical direction in addition to the object pixel, as the intensity of the object pixel is performed, and as the minimum filter processing, processing of setting the minimum intensity at n pixels, including temporally-previous n−1 pixels in the vertical direction in addition to the object pixel, as the intensity of the object pixel is performed.

In this way, by executing the maximum and minimum filter processing by use of n pixels that temporally-previous n−1 pixels in the vertical direction are added to the object pixel, it is possible to favorably suppress extraction of a fake difference image component. Further, in this case, the number of pixels n used for the maximum filter processing and the minimum filter processing is preferably set to an integer of 3 or more and 5 or less.

Further, the fluorescence observation device may use a configuration in which, in the filter processing means, as the maximum filter processing, with m being an integer of 2 or more, processing of setting the maximum intensity at m pixels, including m−1 pixels in the horizontal direction in addition to the object pixel, as the intensity of the object pixel is performed, and as the minimum filter processing, processing of setting the minimum intensity at m pixels, including m−1 pixels in the horizontal direction in addition to the object pixel, as the intensity of the object pixel is performed.

In the same way, the fluorescence observation method may use a configuration in which, in the filter processing step, as the maximum filter processing, with m being an integer of 2 or more, processing of setting the maximum intensity at m pixels, including m−1 pixels in the horizontal direction in addition to the object pixel, as the intensity of the object pixel is performed, and as the minimum filter processing, processing of setting the minimum intensity at m pixels, including m−1 pixels in the horizontal direction in addition to the object pixel, as the intensity of the object pixel is performed.

In this way, in accordance with the configuration in which the maximum and minimum filter processing are performed by use of m pixels that m−1 pixels in the horizontal direction are added to the object pixel, for example, in the case where there is a movement of the object, or the like, it is possible to favorably suppress extraction of a fake difference image component.

The fluorescence observation device may use a configuration which includes distribution image generating means for generating an intensity distribution image showing fluorescence intensity distribution based on the difference image output from the difference image generating means. In the same way, the fluorescence observation method may use a configuration which includes a distribution image generating step of generating an intensity distribution image showing fluorescence intensity distribution based on the difference image output in the difference image generating step.

In this way, the difference image in which fluorescence is extracted is not directly used, but is converted into an intensity distribution image, to be used for fluorescence observation, thereby it is possible to efficiently carry out, for example, visual check of an observation image of faint fluorescence, and the like. Further, in the case where an intensity distribution image is generated to be used in this way, specifically, for example, the configuration in which a single or a plurality of threshold values are applied to the difference image, to generate a binarized image or a colorized image serving as the intensity distribution image may be used.

Further, the fluorescence observation device may use a configuration which includes superimposed image generating means for generating a superimposed image in which the fluorescence image or the background image output from the imaging device, and the intensity distribution image output from the distribution image generating means are superimposed. In the same way, the fluorescence observation method may use a configuration which includes a superimposed image generating step of generating a superimposed image in which the fluorescence image or the background image output from the imaging device, and the intensity distribution image output in the distribution image generating step are superimposed.

In this way, in accordance with the configuration in which a superimposed image, in which an original fluorescence image or background image and an intensity distribution image such as a binarized image or a colorized image are superimposed, is used for fluorescence observation, efficient fluorescence observation of the object is possible in various manners, such as, for example, being possible to visually check a generating position of fluorescence in the object from an observation image.

INDUSTRIAL APPLICABILITY

The present invention is available for a fluorescence observation device and a fluorescence observation method which are capable of generating images in which fluorescence is extracted in real time in a configuration of acquiring fluorescence observation images of an object in time series.

REFERENCE SIGNS LIST 1A, 1B, 1C—fluorescence observation device, 10—observing object, 11—observation light source (excitation light supplying means), 12—interlaced imaging device, 13—motion sensor, 15—field memory (image storage means),
20—difference computing unit (difference image generating means), 21—MAX/MIN filter (filter processing means), 22—line memory, 25—switching signal generating unit, 30—distribution image generating unit (distribution image generating means), 31—threshold value setting unit, 32—comparator, 33—image converting unit, 35—multiplexer (superimposed image generating means), 50—display device.

The invention claimed is:

1. A fluorescence observation device comprising:
an excitation light source configured to supply excitation light for fluorescence observation of an observing object and capable of switching between ON/OFF of the excitation light supply;
an interlaced imaging sensor configured to take an optical image from the observing object, and alternately output first field images and second field images in time series as obtained image data of the observing object;
an image storage configured to store the first field images or the second field images output from the imaging sensor; and
a difference image generator configured to generate a difference image obtained by a difference between one of the first field images and the second field images output from the imaging sensor, and the other of the first field images and the second field images stored in the image storage;
a switching signal generator configured to generate a switching signal switching in synchronization with a first field image acquiring period and a second field image acquiring period based on a signal from the imaging sensor, wherein
the excitation light source supplies the excitation light such that one of the first field image acquiring period and the second field image acquiring period by the imaging sensor is to be a period in which the excitation light supply is turned ON to acquire a fluorescence image, and the other is to be a period in which the excitation light supply is turned OFF to acquire a background image, and
the difference image generator, as its generation mode, switches between (i) a first mode of, in a case where the fluorescence image is output from the imaging sensor, generating the difference image by subtracting the background image, which is acquired in advance of the fluorescence image to be stored in the image storage, from the fluorescence image, and (ii) a second mode of, in a case where the background image is output from the imaging sensor, generating the difference image by subtracting the background image from the fluorescence image, which is acquired in advance of the background image to be stored in the image storage, to apply the mode, and
the difference image generator switches between the first mode and the second mode based on the switching signal to apply the mode.

2. A fluorescence observation device, comprising:
an excitation light source configured to supply excitation light for fluorescence observation of an observing object and capable of switching between ON/OFF of the excitation light supply;
an interlaced imaging sensor configured to take an optical image from the observing object, and alternately output first field images and second field images in time series as obtained image data of the observing object;
an image storage configured to store the first field images or the second field images output from the imaging sensor; and
a difference image generator configured to generate a difference image obtained by a difference between one of the first field images and the second field images output from the imaging sensor, and the other of the first field images and the second field images stored in the image storage;
a filter configured to perform, for the intensities of respective pixels contained in the image which is the fluorescence image or the background image output from the image storage to the difference image generator, maximum filter processing of setting the maximum intensity at a plurality of pixels including pixels within a predetermined range in the vicinity of an object pixel in addition to the object pixel, as the intensity of the object pixel, or minimum filter processing of setting the minimum intensity at a plurality of pixels including pixels within a predetermined range in the vicinity of an object pixel in addition to the object pixel, as the intensity of the object pixel, wherein
the excitation light source supplies the excitation light such that one of a first field image acquiring period and a second field image acquiring period by the imaging sensor is to be a period in which the excitation light supply is turned ON to acquire a fluorescence image, and the other is to be a period in which the excitation light supply is turned OFF to acquire a background image, and the difference image generator, as its generation mode, switches between (i) a first mode of, in a case where the fluorescence image is output from the imaging sensor, generating the difference image by subtracting the background image, which is acquired in advance of the fluorescence image to be stored in the image storage, from the fluorescence image, and (ii) a second mode of, in a case where the background image is output from the imaging sensor, generating the difference image by subtracting the background image from the fluorescence image, which is acquired in advance of the background image to be stored in the image storage, to apply the mode, and
the filter switches between the maximum filter processing and the minimum filter processing in the first mode in which the background image is output from the image storage, and in the second mode in which the fluorescence image is output from the image storage, to apply the processing.

3. The fluorescence observation device according to claim 2, comprising a switching signal generator configured to generate a switching signal switching in synchronization with the first field image acquiring period and the second field image acquiring period based on a signal from the imaging sensor, wherein
the difference image generator switches between the first mode and the second mode based on the switching signal to apply the mode, and the filter switches between the maximum filter processing and the minimum filter processing in the first mode and the second mode based on the switching signal to apply the processing.

4. The fluorescence observation device according to claim 2, comprising second image storage configured to store line image data of scanning lines containing the pixels within the predetermined range in the vicinity of the object pixel, with respect to line image data of a scanning line containing the object pixel.

5. The fluorescence observation device according to claim 2, wherein, in the filter,
as the maximum filter processing, with n being an integer of 2 or more, processing of setting the maximum intensity at n pixels including temporally-previous n−1 pixels in the vertical direction in addition to the object pixel, as the intensity of the object pixel is performed, and as the minimum filter processing, processing of setting the minimum intensity at n pixels including temporally-previous n−1 pixels in the vertical direction in addition to the object pixel, as the intensity of the object pixel is performed.

6. The fluorescence observation device according to claim 5, wherein, in the filter, the number of pixels n used for the maximum filter processing and the minimum filter processing is set to an integer of 3 or more and 5 or less.

7. The fluorescence observation device according to claim 1, comprising a distribution image generator configured to generate an intensity distribution image showing fluorescence intensity distribution based on the difference image output from the difference image generator.

8. The fluorescence observation device according to claim 7, wherein the distribution image generator applies a single or a plurality of threshold values to the difference image to generate a binarized image or a colorized image serving as the intensity distribution image.

9. A fluorescence observation device, comprising:
an excitation light source configured to supply excitation light for fluorescence observation of an observing object and be capable of switching between ON/OFF of the excitation light supply;
an interlaced imaging sensor configured an optical image from the observing object, and alternately output first field images and second field images in time series as obtained image data of the observing object;
an image storage configured to store the first field images or the second field images output from the imaging sensor;
a difference image generator configured to generate a difference image obtained by a difference between one of the first field images and the second field images output from the imaging sensor, and the other of the first field images and the second field image stored in the image storage;
a distribution image generator configured to generate an intensity distribution image showing fluorescence intensity distribution based on the difference image output from the difference image generator; and
a superimposed image generator configured to generate a superimposed image in which the fluorescence image or the background image output from the imaging sensor, and the intensity distribution image output from the distribution image generator are superimposed, wherein
the excitation light source supplies the excitation light such that one of the first field image acquiring period and the second field image acquiring period by the imaging sensor is to be a period in which the excitation light supply is turned ON to acquire a fluorescence image, and the other is to be a period in which the excitation light supply is turned OFF to acquire a background image, and the difference image generator, as its generation mode, switches between (i) a first mode of, in a case where the fluorescence image is output from the imaging sensor, generating the difference image by subtracting the background image, which is acquired in advance of the fluorescence image to be stored in the image storage, from the fluorescence image, and (ii) a second mode of, in a case where the background image is output from the imaging sensor, generating the difference image by subtracting the background image from the fluorescence image, which is acquired in advance of the background image to be stored in the image storage, to apply the mode.

10. A fluorescence observation method which uses a fluorescence observation device including
an excitation light source configured to supply excitation light for fluorescence observation of an observing object and capable of switching between ON/OFF of the excitation light supply,
an interlaced imaging sensor configured to take an optical image from the observing object, and alternately output first field images and second field images in time series as obtained image data of the observing object, and
an image storage configured to store the first field images or the second field images output from the imaging sensor,
the method comprising:
generating a difference image obtained by a difference between one of the first field images and the second field images output from the imaging sensor, and the other of the first field images and the second field images stored in the image storage;
supplying the excitation light such that one of a first field image acquiring period and a second field image acquiring period by the imaging sensor is to be a period in which the excitation light supply is turned ON to acquire a fluorescence image, and the other is to be a period in which the excitation light supply is turned OFF to acquire a background image; and
a distribution image generation step of generating an intensity distribution image showing fluorescence intensity distribution based on the difference image output in the difference image generating step, wherein
the difference image generating step, as its generation mode, switches between
a first mode of, in a case where the fluorescence image is output from the imaging sensor, generating the difference image by subtracting the background image, which is acquired in advance of the fluorescence image to be stored in the image storage, from the fluorescence image, and
a second mode of, in a case where the background image is output from the imaging sensor, generating the difference image by subtracting the background image from the fluorescence image, which is acquired in advance of the background image to be stored in the image storage, to apply the mode.

11. The fluorescence observation method according to claim 10, comprising a filter processing step of performing, for the intensities of respective pixels contained in the image which is the fluorescence image or the background image output from the image storage, maximum filter processing of setting the maximum intensity at a plurality of pixels including pixels within a predetermined range in the vicinity of an object pixel in addition to the object pixel, as the intensity of the object pixel, or minimum filter processing of setting the minimum intensity at a plurality of pixels including pixels within a predetermined range in the vicinity of an object pixel in addition to the object pixel, as the intensity of the object pixel, wherein the filter processing step switches between the maximum filter processing and the minimum filter processing in the first mode in which the background image is output from the image storage, and in the second mode in which the fluorescence image is output from the image storage, to apply the processing.

12. The fluorescence observation method according to claim 10, wherein the distribution image generating step applies a single or a plurality of threshold values to the difference image to generate a binarized image or a colorized image serving as the intensity distribution image.

13. The fluorescence observation method according to claim 10, comprising a superimposed image generating step of generating a superimposed image in which the fluorescence image or the background image output from the imaging sensor, and the intensity distribution image output in the distribution image generating step are superimposed.

14. A method of capturing a fluorescence image of an observing object, the method comprising:

by an interlaced imaging sensor, alternately outputting first field images and second field images in time series as image data;

by an image storage, storing at least one of the first field image and the second field image;

by an excitation light source, supplying excitation light such that one of a first field image acquiring period and a second field image acquiring period by the imaging sensor is to be a period in which the excitation light supply is turned ON to acquire a fluorescence image, and the other is to be a period in which the excitation light supply is turned OFF to acquire a background image;

generating a difference image obtained by a difference between one of the first field images and the second field images, and the other of the first field images and the second field images stored in the image storage; and generating an intensity distribution image showing fluorescence intensity distribution based on the difference image, wherein the difference image generating step, as its generation mode, switches between a first mode of in a case where the fluorescence image is output from the imaging sensor, generating the difference image by subtracting the background image, which is acquired in advance of the fluorescence image to be stored in the image storage, from the fluorescence image, and a second mode of, in a case where the background image is output from the imaging sensor, generating the difference image by subtracting the background image from the fluorescence image, which is acquired in advance of the background image to be stored in the image storage, to apply the mode.

15. The method according to claim 14, wherein the distribution image generating step applies a single or a plurality of threshold values to the difference image to generate a binarized image or a colorized image serving as the intensity distribution image.

16. The method according to claim 14, further comprising: superimposing the fluorescence image or the background image, and the intensity distribution image.

* * * * *